US012760346B2

(12) United States Patent
Zhou et al.

(10) Patent No.: US 12,760,346 B2
(45) Date of Patent: Oct. 13, 2026

(54) **RECOMBINANT *ESCHERICHIA coli* FOR EXPRESSING SYNTHESIS PATHWAY OF ASIATICOSIDE AND APPLICATION THEREOF**

(71) Applicant: Jiangnan University, Wuxi (CN)

(72) Inventors: Jingwen Zhou, Wuxi (CN); Weizhu Zeng, Wuxi (CN); Xingying Zhao, Wuxi (CN); Sha Xu, Wuxi (CN); Jian Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 249 days.

(21) Appl. No.: 18/414,523

(22) Filed: Jan. 17, 2024

(65) Prior Publication Data

US 2024/0301461 A1 Sep. 12, 2024

(30) Foreign Application Priority Data

Jan. 17, 2023 (CN) ......................... 202310067492.5
Jan. 17, 2023 (CN) ......................... 202310081810.3

(51) Int. Cl.

| | |
|---|---|
| ***C12P 19/48*** | (2006.01) |
| ***C12N 1/205*** | (2026.01) |
| ***C12N 9/10*** | (2006.01) |
| ***C12R 1/19*** | (2006.01) |

(52) U.S. Cl.

CPC ............ *C12P 19/485* (2013.01); *C12N 1/205* (2021.05); *C12N 9/1051* (2013.01); *C12N 2527/00* (2013.01); *C12R 2001/19* (2021.05)

(58) Field of Classification Search

None

See application file for complete search history.

(56) References Cited

U.S. PATENT DOCUMENTS

2023/0212625 A1* 7/2023 Travers .................. C12P 17/06 435/125

* cited by examiner

*Primary Examiner* — Blaine Lankford

(74) *Attorney, Agent, or Firm* — IPRO, PLLC; Na Xu

(57) ABSTRACT

The present disclosure discloses recombinant *Escherichia coli* for expressing a synthesis pathway of asiaticoside and application thereof, and belongs to the field of bioengineering. Rhamnosyltransferase with an amino acid sequence shown in any one of SEQ ID NO: 25 to SEQ ID NO: 29, glucosyltransferase with an amino acid sequence shown in any one of SEQ ID NO: 10 to SEQ ID NO: 17 and UGT73AH1 reported in a document are transferred into *E. coli* BL21 (DE3)Δpgi to realize co-expression. Fermentation results show that all 5 rhamnosyltransferases screened in the present disclosure can achieve effects, and a unique new peak appears at 0.596 min, which is consistent with a characteristic ion flow of an asiaticoside standard product. According to the present disclosure, barriers of the prior art are broken through, a new biosynthesis method for asiaticoside is provided, and industrialization of biosynthesis of asiaticoside becomes possible.

12 Claims, 9 Drawing Sheets

Specification includes a Sequence Listing.

RECOMBINANT *ESCHERICHIA coli* FOR EXPRESSING SYNTHESIS PATHWAY OF ASIATICOSIDE AND APPLICATION THEREOF

REFERENCE TO SEQUENCE LISTING

The instant application contains a Sequence Listing in XML format as a file named "YGHY-2023-51-SEQ.xml", created on Jan. 12, 2024, of 90.4 kB in size, and which is hereby incorporated by reference in its entirety.

TECHNICAL FIELD

The present disclosure relates to recombinant *Escherichia Coli* for expressing a synthesis pathway of asiaticoside and application thereof, and belongs to the field of bioengineering.

BACKGROUND

As a dry whole herb of umbelliferae plants, *Centella asiatica* includes the chemical components of triterpene saponins, triterpenic acids, polyalkynenes, volatile oils and the like. Moreover, the *Centella asiatica* is rich in a variety of bioactive substances, including the main components of triterpenoids and saponin compounds thereof, asiaticoside B, madecassoside and asiaticoside.

Triterpenoid compounds have been widely found in fungi, ferns, monocotyledons, dicotyledons and animals, especially in dicotyledons. The main bioactive substances of leaf extracts of the *Centella asiatica* are the saponins. The asiaticoside has a wide range of biological activities, such as resistance to cancer, resistance to inflammation, promotion of wound healing, resistance to diabetes mellitus, resistance to oxidation, liver protection, resistance to hepatitis C virus (HCV) and neuroprotection. However, as an important secondary metabolite of plants, the asiaticoside has a complex structure and a relatively low content in plants. In addition, most of these compounds can be mixed with compounds with similar structures. Therefore, it is difficult to obtain a large number of triterpenoid monomers by plant extraction or chemical synthesis, thereby limiting application of the compounds in food, medicine, cosmetic products and other fields. With rapid development of sequencing technologies, more and more enzymes in synthesis pathways of terpenoids have been excavated and identified, and the synthesis pathways of terpenoids have been resolved. In addition, with rapid development of synthetic biology, construction of microbial cell factories to produce the terpenoids and other compounds with great medical values has become a research hotspot.

In the past few decades, relatively little progress has been made on functional characterization of a gene UGT involved in biosynthesis of the triterpenoid compounds, which may be related to plant genomes capable of encoding a large number of UGT homologues. At present, synthesis pathways of the asiaticoside have not been fully resolved, and it is believed through research that the asiaticoside is prepared from asiatic acid by glycosylation in three steps. It is reported by Costa et al. that UGT73AD1 has the effect of connecting a carboxyl group of glucose in *Centella asiatica*, and it is determined through in vitro expression that the UGT73AD1 can be used for specifically glycosylating asiatic acid and madecassic acid. According to Kim et al., glycosyltransferase UGT73AH1 is identified from *Centella asiatica* (L.) Urban, and the enzyme can be used for glycosylating C28-COOH of asiatic acid to produce corresponding monoglycoside. However, whether the enzyme has a catalytic effect on C-2$\alpha$, C-3$\beta$ and C23-OH at other sites is unclear. In addition, glycosyltransferase in last two steps of the three steps for glycosylation is still unknown.

SUMMARY

In the present disclosure, recombinant *E. coli* capable of synthesizing asiaticoside is constructed by subjecting a *Centella asiatica* µlant to second generation transcriptome sequencing, excavating glucosyltransferase and rhamnosyltransferase with potential functions by BLAST comparison, protein modeling, molecular docking, phylogenetic analysis and other bioinformatics means, performing expression verification in *E. coli* and then adding asiatic acid as an exogenous substrate.

The first objective of the present disclosure is to provide application of glucosyltransferase in preparation of asiatico-diglycoside or asiaticoside. The glucosyltransferase is shown in the following (a) or (b):

(a) having an amino acid sequence shown in any one of SEQ ID NO: 10 to SEQ ID NO: 17; and (b) being a protein derived from (a) that is prepared by subjecting the amino acid sequence in (a) to substitution, deletion or addition of one or more of amino acids and has activities of glucosyltransferase.

In one embodiment of the present disclosure, a gene for encoding the glucosyltransferase has a nucleotide sequence shown in any one of SEQ ID NO: 1 to SEQ ID NO: 8.

The second objective of the present disclosure is to provide recombinant *E. coli. E. coli* is used as a host for overexpressing glucosyltransferase and glycosyltransferase UGT73AH1.

In one embodiment of the present disclosure, the glucosyltransferase is shown in the following (a) or (b):

(a) having an amino acid sequence shown in any one of SEQ ID NO: 10 to SEQ ID NO: 17; and (b) being a protein derived from (a) that is prepared by subjecting the amino acid sequence in (a) to substitution, deletion or addition of one or more of amino acids and has activities of glucosyltransferase.

In one embodiment of the present disclosure, the recombinant *E. coli* is obtained by knocking out a gene pgi for encoding a glucose phosphate isomerase protein on a genome.

In one embodiment of the present disclosure, the gene pgi for encoding a glucose phosphate isomerase protein has a nucleotide sequence shown in SEQ ID NO: 18.

In one embodiment of the present disclosure, the glycosyltransferase UGT73AH1 is derived from *Centella asiatica* (L.) Urban.

In one embodiment of the present disclosure, the glycosyltransferase UGT73AH1 has a nucleotide sequence shown in SEQ ID NO: 9 and an amino acid sequence shown in SEQ ID NO: 19.

In one embodiment of the present disclosure, *E. coli* BL21 (DE3) is used as a host for the recombinant *E. coli.*

In one embodiment of the present disclosure, the recombinant *E. coli* is used for overexpressing rhamnosyltransferase with an amino acid sequence shown in any one of SEQ ID NO: 25 to SEQ ID NO: 29.

In one embodiment of the present disclosure, the recombinant *E. coli* is used for expressing rhamnosyltransferase with pRSFDuet-1 as a vector and co-expressing glucosyltransferase and glycosyltransferase UGT73AH1 with pET-Duet-1.

In one embodiment of the present disclosure, *E. coli* BL21 (DE3) is used as a host for the recombinant *E. coli*.

The third objective of the present disclosure is to provide application of the recombinant *E. coli* in synthesis of asiaticodiglycoside or asiaticoside.

The fourth objective of the present disclosure is to provide a method for producing asiaticodiglycoside. The method includes inoculating a seed liquid of the recombinant *E. coli* into a fermentation culture medium, performing shaking culture at 200-240 rpm at 35-38° C. until an $OD_{600}$ value is 0.6-0.8, adding isopropyl thiogalactoside to a final concentration of 0.4-0.6 μmol/L, adding asiatic acid with a final concentration of 150-250 mg/L after 4-8 h, and then performing shaking culture continuously at 200-240 rpm at 28-32° C. for 40-60 h;

or with glucosyltransferase and glycosyltransferase UGT73AH1 as a catalyst, carrying out a reaction in a reaction solution containing uridine diphosphate glucose (UDPG) as a glycosyl donor with a final concentration of 0.8-1.2 g/L and asiatic acid as a substrate with a concentration of 150-250 mg/L at 35-38° C. for 4-10 h.

In one embodiment of the present disclosure, the fermentation culture medium includes 15-25 g/L of glucose, 4-6 g/L of glycerol, 14-18 g/L of $K_2HPO_4 \cdot 3H_2O$, 1-3 g/L of $KH_2PO_4$, 20-30 g/L of yeast powder and 10-15 g/L of peptone.

In one embodiment of the present disclosure, the glucosyltransferase is shown in the following (a) or (b):

(a) having an amino acid sequence shown in any one of SEQ ID NO: 10 to SEQ ID NO: 17; and (b) being a protein derived from (a) that is prepared by subjecting the amino acid sequence in (a) to substitution, deletion or addition of one or more of amino acids and has activities of glucosyltransferase.

In one embodiment of the present disclosure, the glycosyltransferase UGT73AH1 is derived from *Centella asiatica* (L.) Urban.

In one embodiment of the present disclosure, the glycosyltransferase UGT73AH1 has an amino acid sequence shown in SEQ ID NO: 19.

The fifth objective of the present disclosure is to provide application of rhamnosyltransferase in synthesis of asiaticoside or a product containing asiaticosid.

In one embodiment of the present disclosure, the rhamnosyltransferase is shown in the following (a) or (b):

(a) having an amino acid sequence shown in any one of SEQ ID NO: 25 to SEQ ID NO: 29; and (b) being a protein derived from (a) that is prepared by subjecting the amino acid sequence in (a) to substitution, deletion or addition of one or more of amino acids and has activities of glucosyltransferase.

In one embodiment of the present disclosure, a gene for encoding the rhamnosyltransferase has a nucleotide sequence shown in any one of SEQ ID NO: 20 to SEQ ID NO: 24.

The present disclosure has the following beneficial effects.

(1) According to the present disclosure, genes for encoding glucosyltransferase that are screened by transcriptome sequencing of *Centella asiatica* are linked to an *E. coli* expression vector pETDuet-1, respectively, followed by induced expression with an *E. coli* host BL21 (DE3)Δpgi. Induction is performed with 0.5 μmol/L of isopropyl thiogalactoside (IPTG) at 16° C. for 20 h, and cells are collected and subjected to ultrasonic crushing. SDS-PAGE results show that all 8 glucosyltransferases can be expressed normally. Genes for encoding rhamnosyltransferase that are screened from a transcriptome of *Centella asiatica* are linked to an *E. coli* expression vector pRSFDuet-1, respectively, followed by induced expression with an *E. coli* host BL21 (DE3)Δpgi. Induction is performed with 0.5 μmol/L of IPTG at 20° C. for 20 h, and cells are collected and subjected to ultrasonic crushing. SDS-PAGE results show that all 5 rhamnosyltransferases can be expressed normally.

(2) The screened genes for encoding the 8 glucosyltransferases are linked to an *E. coli* expression vector pETDuet-1, respectively, meanwhile, glucosyltransferase UGT73AH1 with a C-28 site reported in a document is linked to an *E. coli* expression vector pET28a, and recombinant *E. coli* is constructed with *E. coli* BL21 (DE3)Δpgi as a host. Induced expression is performed under certain culture conditions, and shake flask fermentation is performed with an empty vector pETDuet-1 as a blank control. 20 g/L of glucose and asiatic acid as a substrate with a final concentration of 200 mg/L are added into a TB culture medium, and samples are collected and detected at 24 h. As can be seen from mass spectrograms, when UGT73AH1, UGT73C7 and UGT73C8 are transferred into the strain BL21 (DE3)Δpgi at the same time, a new peak different from that of the blank control appears at 7.92 min, and mass spectrum data same as that of asiaticodiglycoside are obtained, determining that asiaticodiglycoside is produced in a fermentation solution.

(3) The screened genes for encoding the 8 glucosyltransferases are linked to an *E. coli* expression vector pETDuet-1, respectively, and recombinant *E. coli* is constructed with *E. coli* BL21 (DE3)Δpgi as a host. Induced expression is performed under certain culture conditions with an empty vector pETDuet-1 as a blank control, induction is performed with 0.5 μmol/L of IPTG at 16° C. for 20 h, and cells are collected and subjected to ultrasonic crushing to obtain a crude enzyme solution. The volume of the total enzyme reaction system is 500 μl, the volume of the crude enzyme solution is 100 μl, the final concentration of the added UDPG is 1 g/L, the final concentration of asiatic acid added as a substrate is 200 mg/L, and the system is supplemented with a PBS buffer solution to 500 μl to carry out a reaction at 37° C. for 6 h. As can be seen from mass spectrograms, when UGT73AH1, UGT73C7 and UGT73C8 are transferred into the strain BL21 (DE3)Δpgi at the same time, a new peak different from that of the blank control appears at 7.92 min, and mass spectrum data same as that of asiaticodiglycoside are obtained, determining that asiaticodiglycoside is produced in a reaction solution.

(4) According to the present disclosure, the genes for encoding the 5 rhamnosyltransferases that are screened from a transcriptome of *Centella asiatica* and rhamnose isomerase VvRHM derived from *Vitis vinifera* are linked to an *E. coli* expression vector pRSFDuet-1, respectively, and glucosyltransferase UGT73AH1 with a C-28 site reported in a document and glucosyltransferase UGT73 (UGT73C7 or UGT73C8) are linked to an *E. coli* expression vector pETDuet-1 and transferred into an *E. coli* host BL21 (DE3)Δpgi to construct recombinant *E. coli*. The recombinant *E. coli* is inoculated into a TB culture medium containing 20 g/L of glucose, where the final concentration of asiatic acid added as a substrate is 200 mg/L. After induced expression, samples are collected and detected at 24 h. As can be seen from mass spectrograms, all the 5 rhamnosyltransferases screened from the transcriptome can achieve effects, and a unique new peak appears at 0.596 min, which is consistent with a characteristic ion flow of an asiaticoside standard product. According to the present disclosure, barriers of the prior art are broken through, a new biosynthesis method for asiaticoside is provided, and industrialization of biosynthesis of asiaticoside becomes possible.

BRIEF DESCRIPTION OF FIGURES

FIG. 5 shows SDS-PAGE electrophoresis results of recombinant *E. coli* RRT in expression.

DETAILED DESCRIPTION (One) Culture Media

Figure 1A:
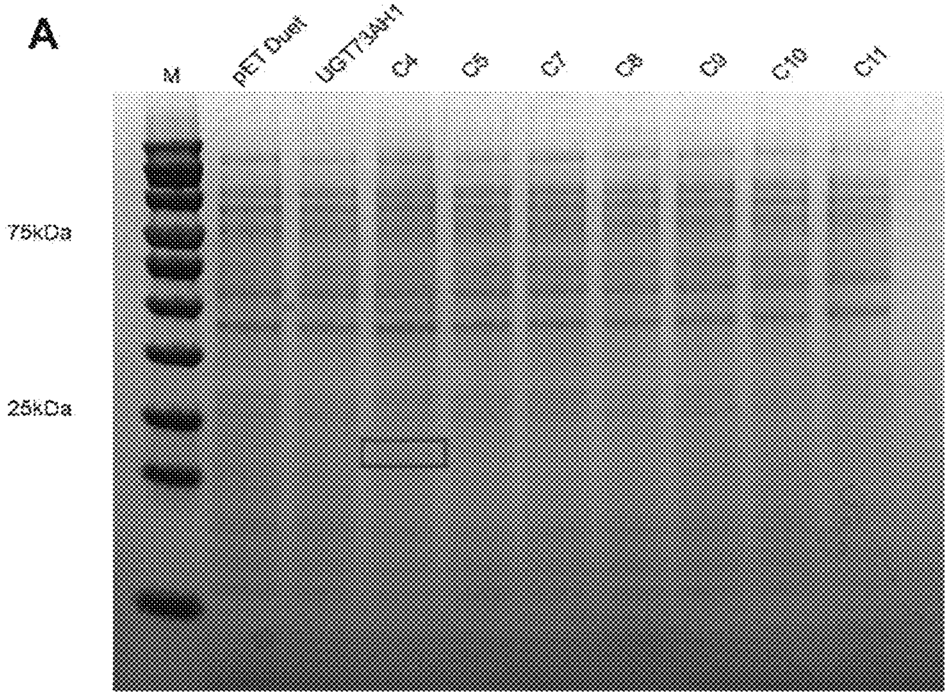
FIG. 1 shows SDS-PAGE electrophoresis results of recombinant *E. coli* UGT73 in expression, where FIG. A shows a supernatant, and FIG. B shows a precipitate.

A seed culture medium (LB) includes: 10 g/L of peptone, 5 g/L of a yeast extract and 5 g/L of sodium chloride; and 2% (mass fraction) of agar powder was added into a solid culture medium.

A fermentation culture medium (TB) includes: 20 g/L of glucose, 5 g/L glycerol, 16.4 g/L of $K_2HPO_4 \cdot 3H_2O$, 2.31 g/L of $KH_2PO_4$, 24 g/L of yeast powder and 12 g/L of peptone. 20 g/L of the glucose was sterilized separately and mixed uniformly before inoculation.

(Two) PCR Reaction System and Amplification Conditions

1 μL (10 μM) of a forward primer, 1 μL (10 μM) of a reverse primer, 20 ng of template DNA and 25 μL of 2×Phanta Max Master Mix were used, and double distilled water was added to 50 μL. Amplification conditions were as follows: pre-denaturation at 95° C. for 3 min, followed by 30 cycles (at 95° C. for 15 s, at 55° C. for 15 s and at 72° C. for 15 s) and continuous extension at 72° C. for 10 min.

(Three) Preparation of *E. coli* Competent Cells

*E. coli* BL21 (DE3) was subjected to gene editing by using a CRISPR/Cas9 system to construct *E. coli* BL21 (DE3)Δpgi. A plasmid pTarget used for knockout was constructed by a PCR mediated point mutation technology, and a template plasmid pTarget were stored in a laboratory. Primers P21pgi-F and P21pgi-R were used for constructing a plasmid pTarget-pgi, and PPGI-UPARM-F/R and PPGI-downARM-F/R were used for constructing homologous arms used for knockout. Specific operation methods are referred to the document: Li Q, Sun B, Chen J, et al. A modified pCas/pTargetF system for CRISPR-Cas9-assisted genome editing in *Escherichia coli* [J]. Acta Biochimica et Biophysica *Sinica*: English version, 2021, 53(5):8.

```
P21pgi-F:
                                          (SEQ ID NO: 64)
AGTTGCTGGCGCTGATTGGCATCGTTTTAGAGCTAGAAATAGCAAGTTA
AAATAAGGCT;

P21pgi-R:
                                          (SEQ ID NO: 65)
AAACGATGCCAATCAGCGCCAGCACTAGTATTATACCTAGGACTGAGCT
AG;

21-PGI-UPARM-F:
                                          (SEQ ID NO: 66)
cctcgtgtcaggggatccattttc;

21-PGI-UPARM-R:
                                          (SEQ ID NO: 67)
tgatccggcaaacaaaccaccgctggtagccacggcgcggttttcagtg
c;

21-PGI-DOWNARM-F:
                                          (SEQ ID NO: 68)
gctaccagcggtggtttgtttgccggatcattgagcaggaatatcgtga
tcagg;

21-PGIDOWNARM-R:
                                          (SEQ ID NO: 69)
tttacccaaaaacatttcgggcg;
```

BL21 (DE3)Δpgi in a glycerol tube was streaked on a corresponding LB plate and cultured overnight at 37° C. (for about 12 h). After 12 h, flat, round and vigorously growing bacteria were selected, inoculated into a 50 mL shake flask containing 5 mL of an LB culture medium and cultured at 220 rpm at 37° C. for about 8-10 h. The bacteria were inoculated into a 250 mL conical flask containing 50 mL of LB at an inoculation amount of 1% and cultured at 220 rpm at 37° C. for about 2 h until an $OD_{600}$ value was 0.6-0.8. A bacterial solution was transferred to a 50 mL centrifuge tube, placed on ice for about 10-15 min and centrifuged at 4,000 rpm at 4° C. for 5 min to remove a supernatant. 5 mL of a solution A was added for resuspension, and centrifugation was performed at 4,000 rpm at 4° C. for 5 min to remove a supernatant. Then, 5 mL of a solution B was added to resuspend the bacteria, and a resulting product was packaged in 100 μL/part and store at −80° C.

(Four) Transformation of *E. coli*

*E. coli* competent cells were thawed on ice. 10 μL of a recombinant product was added into 100 μL of the competent cells and subjected to standing on ice for 30 min. A resulting mixture was subjected to heat shock in a water bath pot at 42° C. for 45 s, followed by standing on ice for 2 min. 1 mL of an LB culture medium was added, and incubation was performed at 220 rpm at 37° C. for 60 min. Then, centrifugation was performed at 4,000 rpm for 2 min to remove 900 μL of a supernatant. The bacteria were resuspended with the remaining culture medium and then coated on a corresponding resistant plate.

(Five) Identification of asiaticodiglycoside: After completion of fermentation, 2 mL of a fermentation solution was taken, added into an equal volume of methanol, violently shaken and uniformly mixed, followed by centrifugation at 14,000 r/min for 10 min. A supernatant was taken and filtered with a 0.22 μm organic phase filter membrane, and a product was identified by UPLC-IT-TOF/MS of Shimadzu.

(Six) Determination of asiaticodiglycoside by high performance liquid chromatography (HPLC): A Thermo Fisher C18 chromatographic column (4.6 mm×250 mm, 5 m) was used for chromatographic separation; the temperature of a column oven was set to 40° C.; the injection volume was 10 μL; mobile phases were as follows: phase A: ultrapure water (0.1% of trifluoroacetic acid was added), and phase B: acetonitrile (0.1% of trifluoroacetic acid was added); the total flow rate was 1 mL/min; isocratic elution was used as an elution method, and the ratio of the phase A to the phase B was 70:30; and the wavelength of a detector was 210 nm.

(Seven) Extraction of asiaticoside: After completion of fermentation, 2 ml of a fermentation solution was taken, added into an equal volume of methanol, violently shaken and uniformly mixed, followed by centrifugation at 14,000 r/min for 10 min. A supernatant was taken and filtered with a 0.22 μm organic phase filter membrane, and a product was detected by UPLC-IT-TOF/MS of Shimadzu.

(Eight) Determination of asiaticoside by HPLC: A Thermo Fisher C18 chromatographic column (4.6 mm×250 mm, 5 m) was used for chromatographic separation; the temperature of a column oven was set to 40° C.; the injection volume was 10 μL; mobile phases were as follows: phase A: ultrapure water (0.1% of trifluoroacetic acid was added), and phase B: acetonitrile (0.1% of trifluoroacetic acid was added); the total flow rate was 1 mL/min; isocratic elution was used as an elution method, and the ratio of the phase A to the phase B was 70:30; and the wavelength of a detector was 210 nm.

Example 1 Screening of Glucosyltransferases with Potential Functions

Through BLAST comparison between data of a transcriptome of *Centella asiatica* and glucosyltransferases with a C-28 site that have known functions and are derived from 17 different sources in documents, results show that 5 isoenzymes are basically homologous to 12 genes with an E value of 0.

Through comparison between sequences of the 12 genes, it can be seen that evm.model.CM025782.1.1646 [mRNA] and reported CaUGT73AH1 have differences in only one amino acid, evm.model.CM025782.1.1645 [mRNA] and evm.model.CM025782.1.1643 [mRNA] have an exactly same protein sequence, and evm.model.CM025782.1.1647 [mRNA] and CaUGT73AH1 have an exactly same protein sequence. In addition, all known glucosyltransferases with C28-COOH reported at present belong to the UGT73 family.

According to KEGG analysis results is combination with BLAST comparison results, the enzymes were renumbered, as shown in Table 1 below.

TABLE 1

Glycosyltransferases with high similarity

| Transcriptome gene ID | Number | Functional annotation of KEGG | Functional annotation of GO |
|---|---|---|---|
| evm.model.CM025782.1.1649 [mRNA] | UGT73C1 | K13496 UGT73C; UDP-glucosyltransferase 73C [EC:2.4.1.-] | GO:0008194(UDP-glycosyltransferase activity) |
| evm.model.CM025782.1.1644 [mRNA] | UGT73C4 | | |
| evm.model.CM025782.1.1643 [mRNA] | UGT73C5 | | |
| evm.model.CM025783.1.1337 [mRNA] | UGT73C7 | | |
| evm.model.CM025783.1.1336 [mRNA] | UGT73C8 | | |
| evm.model.CM025783.1.1338 [mRNA] | UGT73C9 | | |
| evm.model.CM025783.1.1335 [mRNA] | UGT73C10 | ND | |
| evm.model.CM025781.1.1405 [mRNA] | UGT73C11 | ND | |

Example 2 Gene Amplification of Glycosyltransferase and Construction of Recombinant *E. coli* for Expressing Glucosyltransferase With cDNA obtained by reverse transcription of *Centella asiatica* as a template, priming pairs (Table 2) used for amplifying the glucosyltransferases screened in Example 1 were designed and subjected to amplification by PCR, respectively by selecting a Primer Star MasterMix high-fidelity pfu enzyme (Takara) under the following conditions: pre-denaturation at 95° C. for 3 min; at an amplification stage, 30 cycles at 95° C. for 15 s, at 60° C. for 15 s and at 72° C. for 1 min; and extension at 72° C. for 5 min. PCR products were purified to obtain target fragments UGT73C1 to UGT73C11, a vector pETDuet-1 was subjected to amplification by PCR with primers pETDuet-F and pETDuet-R, and a product was purified. The purified fragments UGT73C1 to UGT73C11 were recombined with the vector pETDuet-1 skeleton by a Gibson assembly method to obtain recombinant vectors, respectively, and the recombinant vectors were transferred into *E. coli* JM109. The recombinant vectors obtained were sent to Shanghai Biotech for sequencing to obtain correctly sequenced recombinant plasmids pETDuet-1-UGT73C1, pETDuet-1-UGT73C4, pETDuet-1-UGT73C5, pETDuet-1-UGT73C7, pETDuet-1-UGT73C8, pETDuet-1-UGT73C9, pETDuet-1-UGT73C10 and pETDuet-1-UGT73C11. Then, the plasmids were transferred into *E. coli* BL21 (DE3)Δpgi to obtain recombinant *E. coli* BL21 (DE3)Δpgi/pETDuet-1-UGT73C1 to BL21 (DE3) Δpgi/pETDuet-1-UGT73C11, respectively.

A primer pair (UGT73AH1-F/UGT73AH1-R, Table 2) used for amplifying UGT73AH1 derived from *Centella asiatica* (L.) Urban was designed. With a synthetic sequence as a template, the primer pair was subjected to amplification by PCR by selecting a Primer Star MasterMix high-fidelity pfu enzyme (Takara) under the following conditions: pre-denaturation at 95° C. for 3 min; at an amplification stage, 30 cycles at 95° C. for 15 s, at 56° C. for 15 s and at 72° C.

for 1 min; and extension at 72° C. for 5 min. A PCR product was purified, a vector pET28a was subjected to amplification by PCR with 28a-F and 28a-R, and a product was purified. A purified fragment UGT73AH1 and the vector pET28a skeleton were recombined by a Gibson assembly method to obtain a recombinant vector, and the recombinant vector was transferred into *E. coli* JM109. The obtained vector was sequenced to obtain a correctly sequenced recombinant plasmid pET28a-UGT73AH1, and then the plasmid was transferred into *E. coli* BL21 (DE3)Δpgi to obtain recombinant *E. coli* BL21 (DE3)Δpgi/pET28a-UGT73AH1.

The recombinant plasmids pETDuet-1-UGT73C1 to pETDuet-1-UGT73C11 were transferred into the recombinant *E. coli* BL21 (DE3)Δpgi/pET28a-UGT73AH1, respectively to obtain a series of recombinant bacteria BL21 (DE3)Δpgi/pETDuet-1-UGT73C1/pET28a-UGT73AH1 to BL21 (DE3)Δpgi/pETDuet-1-UGT73C11/pET28a-UGT73AH1 containing UGT73AH1 and the glycosyltransferases screened in Example 1.

Primers used for constructing expression vectors of glucosyltransferases

| Primer | Sequence (5'-3') | |
|---|---|---|
| UGT73C1-F | TAAGAAGGAGATATACCATGACCAGCAGTCAGCTGAAAG | SEQ ID NO: 30 |
| UGT73C1-R | CTGTTCGACTTAAGCATTACTTATTCAGCAGCGGACCCACA | SEQ ID NO: 31 |
| UGT73C4-F | TAAGAAGGAGATATACCATGGATGATCTCTCTTCTCTAAAACTGGGTGTTAAATTTTTTCAAGC | SEQ ID NO: 32 |
| UGT73C4-R | CTGTTCGACTTAAGCATTACTTTCCCTTAACAAACGGCGGACTTCCAC | SEQ ID NO: 33 |
| UGT73C5-F | TTAAGAAGGAGATATACCATGGCTACCAATATTGAGCAGCAGCAGC | SEQ ID NO: 34 |
| UGT73C5-R | TTAAGAAGGAGATATACCATGGCTACCAATATTGAGCAGCAGCAGC | SEQ ID NO: 35 |
| UGT73C7-F | TTAAGAAGGAGATATACCATGGATTCACAATTTCAGCAGCTTCACTTTGTTATGATACCC | SEQ ID NO: 36 |
| UGT73C7-R | CTGTTCGACTTAAGCATTAGCTTAATGCTAACCTATCCTTTACTTGTTCAATGATGTCTTG | SEQ ID NO: 37 |
| UGT73C8-F | TAAGAAGGAGATATACCATGGGTTCAGAATCTCAAGTGCAGCTTCAC | SEQ ID NO: 38 |
| UGT73C8-R | GTTCGACTTAAGCATCACTTCCTTTCTTTCAAAATGTCTTGGATTAGTAACGTC | SEQ ID NO: 39 |
| UGT73C9-F | TAAGAAGGAGATATACCATGGCCAACTTAGCTCAAAACCTTCATTTTGTCTTGC | SEQ ID NO: 40 |
| UGT73C9-R | TTCTGTTCGACTTAAGCATCATTTACTTGTCCCATGGGCCATAATTTCTTGAATTAGGTG | SEQ ID NO: 41 |
| UGT73C10-F | TAAGAAGGAGATATACCATGTCCCGAATCAGCGGTC | SEQ ID NO: 42 |
| UGT73C10-R | TGTTCGACTTAAGCATCAAACATTTTCTTGATTGTTCAATTTCCGG | SEQ ID NO: 43 |
| UGT73C11-F | TAAGAAGGAGATATACCATGGGAACTATTGCAAACGGAGAAATTGCCC | SEQ ID NO: 44 |
| UGT73C11-R | GTTCGACTTAAGCATCAACAAGTGGTAATTGATCTAATTTCTGAAATGAATTCGTCG | SEQ ID NO: 45 |
| UGT73AH1-F | AAGAAGGAGATATACAATGGATTCTCAATTTCAACAATTGCATTTTG | SEQ ID NO: 46 |
| UGT73AH1-R | CAGCAGCCTAGGTTAATttaAGACAAAGCTAATCTATCTTTAACTTGTTCAATTATATCTTG | SEQ ID NO: 47 |
| 28a-R | GTTGAAATTGAGAATCCATggtatatctccttcttaaagttaaacaaaattatttctagaggg | SEQ ID NO: 48 |
| 28a-F | GATAGATTAGCTTTGTCTtaagaattcgagctccgtcgacaag | SEQ ID NO: 49 |
| pETDuet-R | GTATATCTCCTTCTTAAAGTTAAACAAAATTATTTCTAGAGGGG | SEQ ID NO: 50 |
| pETDuet-F | TGCTTAAGTCGAACAGAAAGTAATCGTATTG | SEQ ID NO: 51 |

Example 3 Induced Expression of Glucosyltransferase

With a strain BL21 (DE3)Δpgi/pETDuet-1 transformed with an empty vector pETDuet-1 as a control, the series of recombinant *E. coli* constructed in Example 2 were subjected to streak culture on an LB plate containing ampicillin with a concentration of 50 μg/mL at 37° C. for 12 h, respectively. Single bacterial colonies were selected, transferred into 5 mL of an LB liquid culture medium containing ampicillin with a concentration of 50 μg/mL and subjected to shaking culture at 220 rpm at 37° C. for 12 h. The single bacterial colonies were transferred into 25 mL of a TB liquid culture medium containing ampicillin with a concentration of 50 μg/mL at an inoculation amount of 1% by volume and subjected to shaking culture at 220 rpm at 37° C. until an $OD_{600}$ value was 0.6-0.8. Isopropyl thiogalactoside (IPTG) was added to a final concentration of 0.5 μmol/L and subjected to shaking culture continuously at 220 rpm at 16° C. for 20 h.

Figure 1B:
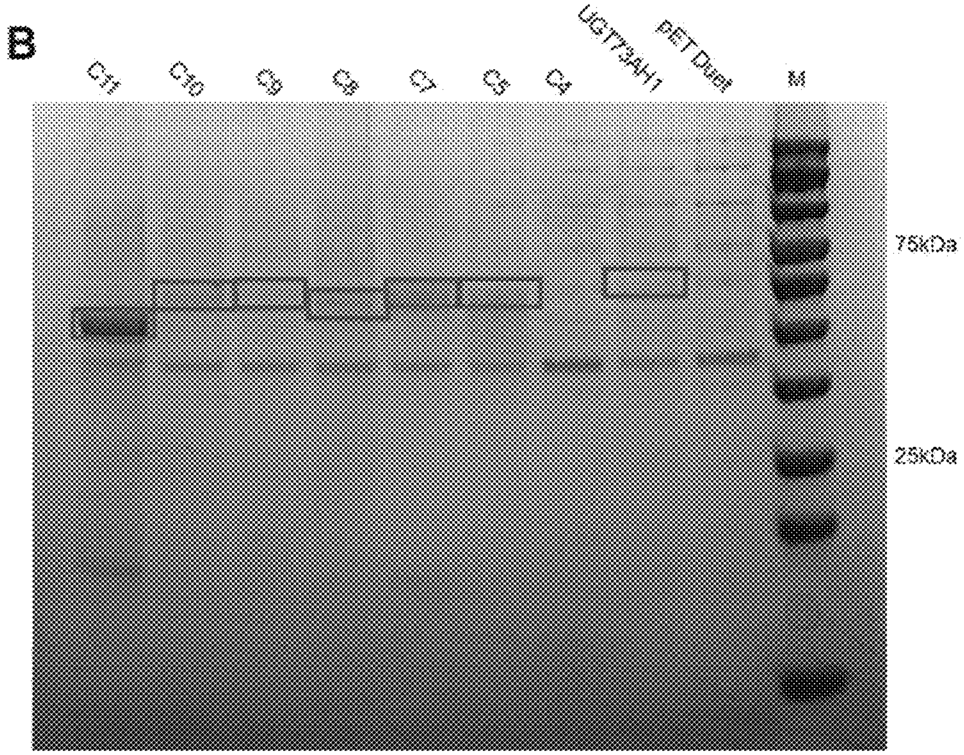
Figure 2A:
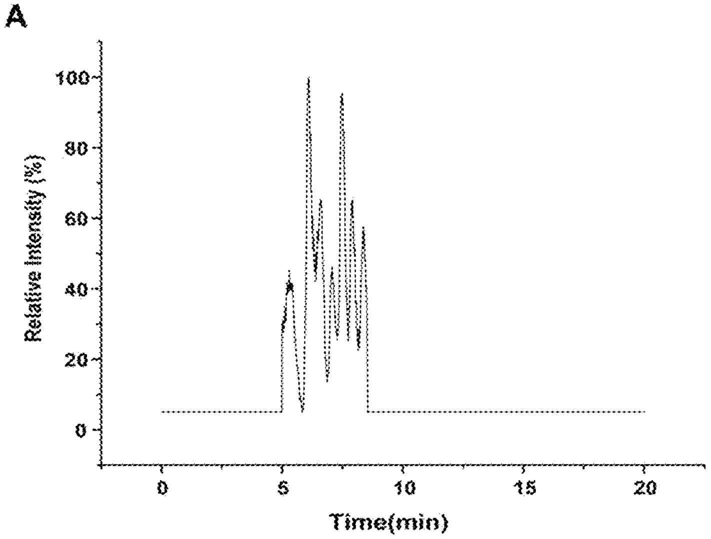
FIG. 2A shows a liquid phase of recombinant *E. coli* UGT73 and UGT73AH1 in shake flask fermentation.
Figure 2B:
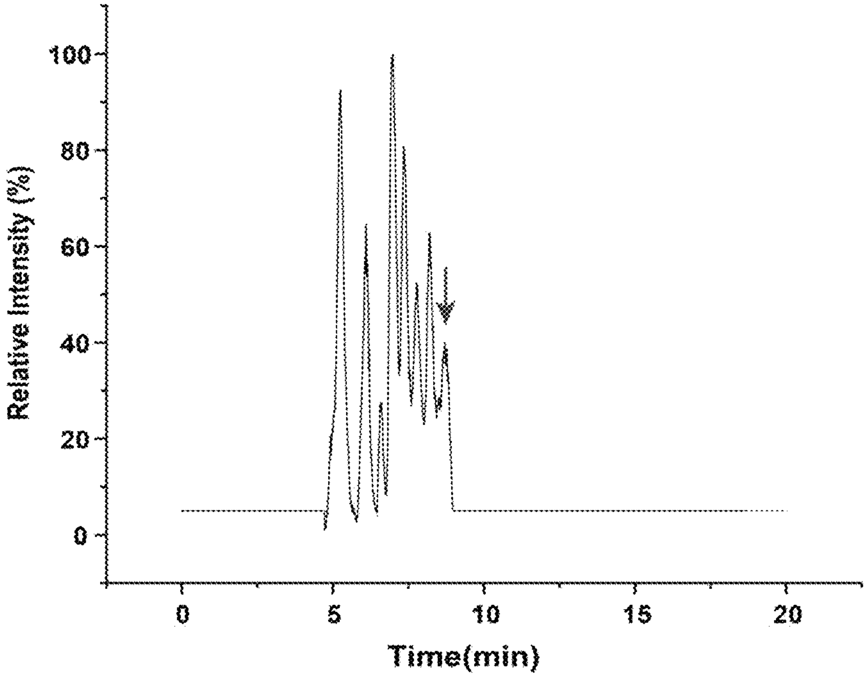
FIG. 2B shows a liquid phase of a UGTs glycosylation product fermented by recombinant *E. coli* UGT73AH1 in shake flask fermentation.
Figure 3A:
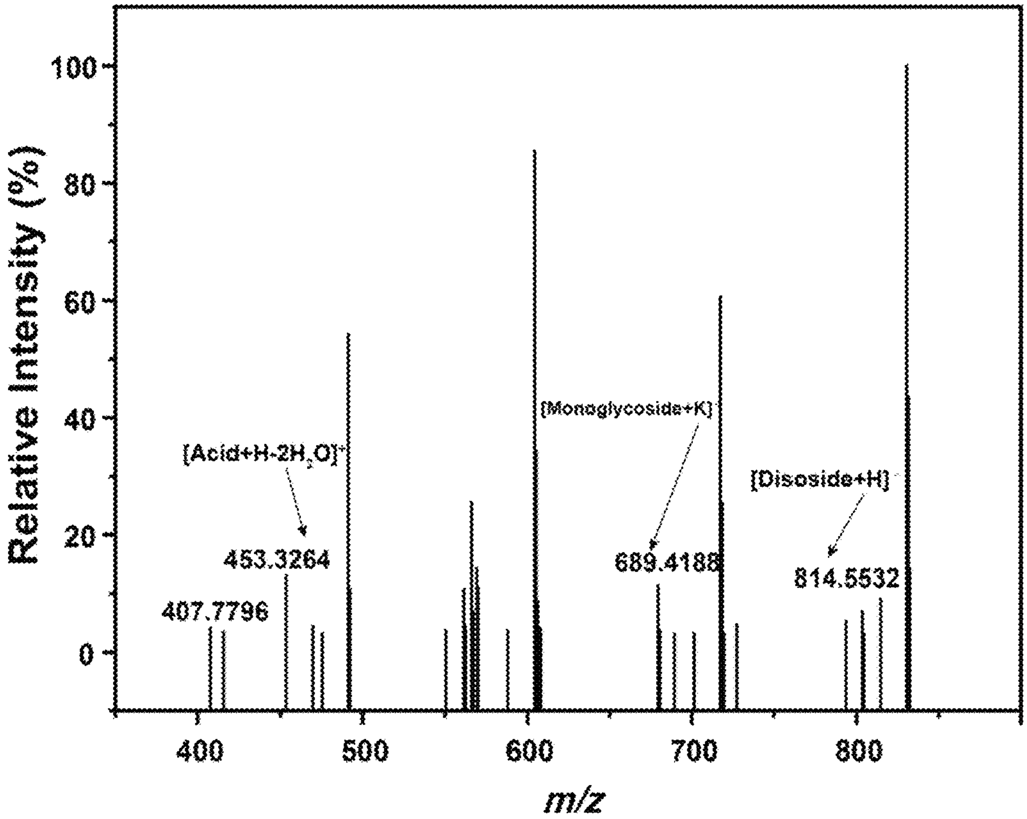
FIG. 3A shows mass spectrograms on positive ion fragments of recombinant *E. coli* UGT73 and UGT73AH1 in shake flask fermentation.
Figure 3B:
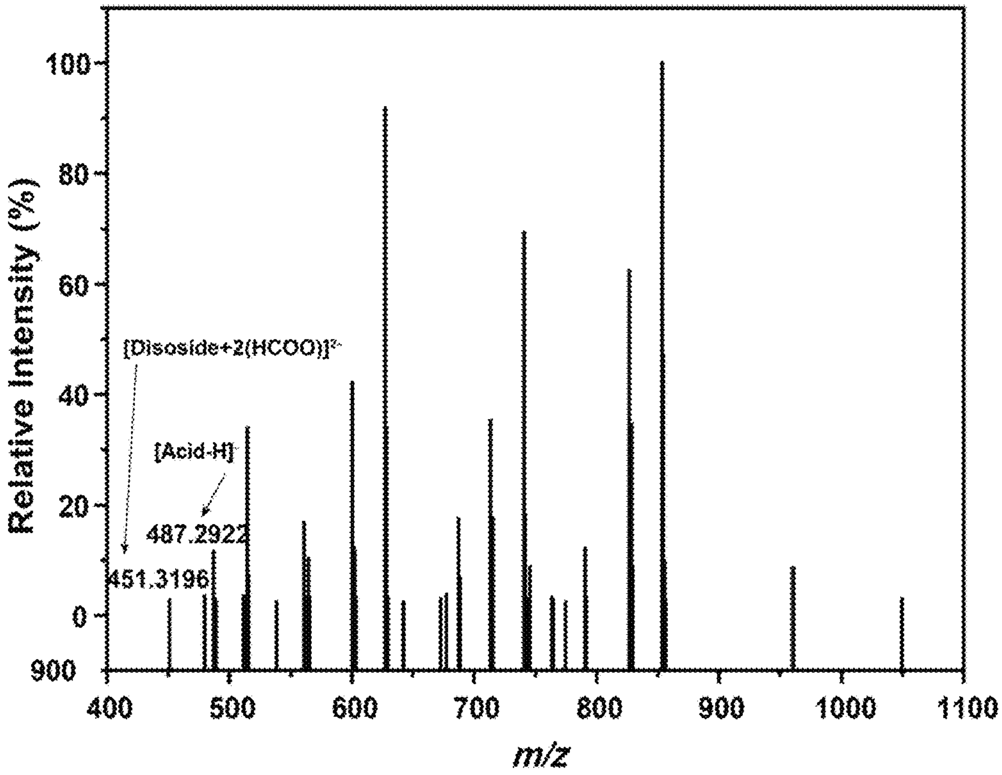
FIG. 3B shows mass spectrograms on negative ion fragments of recombinant *E. coli* UGT73 and UGT73AH1 in shake flask fermentation.

1 mL of a bacterial solution was sucked to determine the final $OD_{600}$ value. 1 mL of the bacterial solution was centrifuged at 5,000×g for 1 min to collect bacteria, and the bacteria were resuspended with 1 mL of a 0.1 M PBS buffer solution with a pH value of 7.4, centrifuged at 5,000×g for 1 min and then washed to remove the residual culture medium. The bacteria were resuspended with a 0.1 M PBS buffer solution with a pH value of 7.4 to control the $OD_{600}$ value of a final resuspended bacterial solution at 5. The bacteria were crushed with an ultrasonic crusher. After completion of crushing, a crushed solution was collected and centrifuged at 12,000×g for 2 min, and a supernatant, namely, a crude enzyme solution of glucosyltransferase, was collected. SDS-PAGE results are shown in FIG. 1.

Example 4 Production of Asiaticodiglycoside by Induced Fermentation of Recombinant *E. coli*

With a strain BL21 (DE3)Δpgi/pETDuet-1/pET28a transformed with an empty vector as a control, the series of recombinant *E. coli* BL21 (DE3)Δpgi/pETDuet-1-UGT73C1/pET28a-UGT73AH1 to BL21 (DE3)Δpgi/pETDuet-1-UGT73C11/pET28a-UGT73AH1 constructed in Example 2 were subjected to streak culture on an LB plate containing kanamycin with a concentration of 50 μg/mL and ampicillin with a concentration of 50 μg/mL at 37° C. for 12 h, respectively. Single bacterial colonies were selected, transferred into 5 mL of an LB liquid culture medium containing kanamycin with a concentration of 50 μg/mL and ampicillin with a concentration of 50 μg/mL and subjected to shaking culture at 220 rpm at 37° C. for 12 h. The single bacterial colonies were transferred into 25 mL of a TB liquid culture medium containing kanamycin with a concentration of 50 μg/mL and ampicillin with a concentration of 50 μg/mL at an inoculation amount of 1% by volume and subjected to shaking culture at 220 rpm at 37° C. until an $OD_{600}$ value was 0.6-0.8. Isopropyl thiogalactoside (IPTG) was added to a final concentration of 0.5 μmol/L, asiatic acid was added as a substrate after 6 h to reach a final concentration of 200 mg/L, shaking culture was performed continuously at 220 rpm at 30° C. for 48 h, and samples were collected and detected at 24 h.

After completion of fermentation, 2 mL of a fermentation solution was taken, added into an equal volume of methanol, violently shaken and uniformly mixed, followed by centrifugation at 14,000 r/min for 10 min. A supernatant was taken and filtered with a 0.22 μm organic phase filter membrane, and a product was detected by UPLC-IT-TOF/MS of Shimadzu. As can be seen from mass spectrograms in FIG. 2A, FIG. 2B, FIG. 3A and FIG. 3B, when UGT73AH1, UGT73C7 and UGT73C8 are transferred into the strain BL21 (DE3)Δpgi at the same time, a new peak different from that of the blank control appears at 7.92 min, and mass spectrum data same as that of asiaticodiglycoside are obtained, determining that asiaticodiglycoside is produced.

Example 5 Production of Asiaticodiglycoside by a Reaction of a Crude Enzyme Solution With a strain BL21 (DE3)Δpgi/pETDuet-1/pET28a transformed with an empty vector as a control, the series of recombinant *E. coli* BL21 (DE3)Δpgi/pETDuet-1-UGT73C1/pET28a-UGT73AH1 to BL21 (DE3)Δpgi/pETDuet-1-UGT73C11/pET28a-UGT73AH1 constructed in Example 2 were subjected to streak culture on an LB plate containing kanamycin with a concentration of 50 μg/mL and ampicillin with a concentration of 50 μg/mL at 37° C. for 12 h, respectively. Single bacterial colonies were selected, transferred into 5 mL of an LB liquid culture medium containing kanamycin with a concentration of 50 μg/mL and ampicillin with a concentration of 50 μg/mL and subjected to shaking culture at 220 rpm at 37° C. for 12 h. The single bacterial colonies were transferred into 25 mL of a TB liquid culture medium containing kanamycin with a concentration of 50 μg/mL and ampicillin with a concentration of 50 μg/mL at an inoculation amount of 1% and subjected to shaking culture at 220 rpm at 37° C. until an $OD_{600}$ value was 0.6-0.8. Isopropyl thiogalactoside (IPTG) was added into a culture to reach a final concentration of 0.5 μmol/L, and shaking culture was performed continuously at 220 rpm at 16° C. for 20 h.

After completion of culture, 1 mL of the culture was sucked to determine the final $OD_{600}$ value. 1 mL of a bacterial solution was centrifuged at 5,000×g for 1 min to collect bacteria. The bacteria were resuspended with 1 mL of a 0.1 M PBS buffer solution with a pH value of 7.4, centrifuged at 5,000×g for 1 min and then washed to remove the residual culture medium. The bacteria were resuspended with a 0.1 M PBS buffer solution with a pH value of 7.4 to control the $OD_{600}$ value of a final resuspended bacterial solution at 5. The bacteria were crushed with an ultrasonic crusher. After completion of crushing, a crushed solution was collected and centrifuged at 12,000×g for 2 min, and a supernatant, namely, a crude enzyme solution of glucosyltransferase, was collected.

Figure 4A:
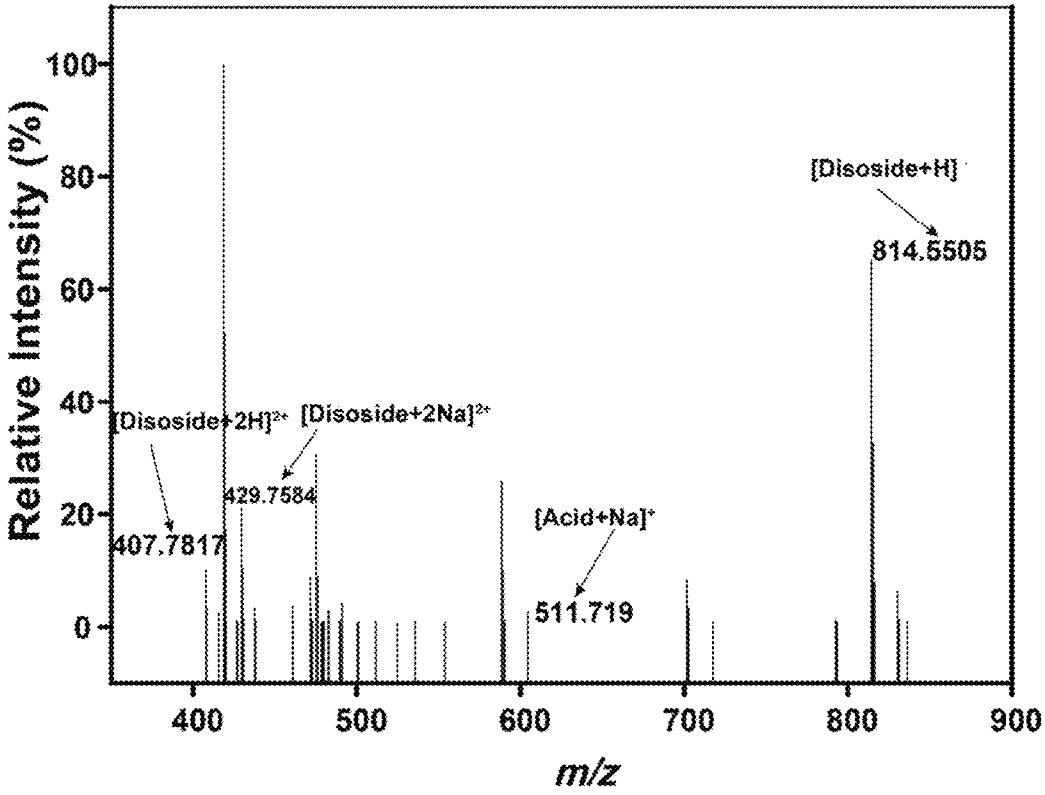
FIG. 4A shows mass spectrograms on positive ion fragments of crude enzyme solutions of recombinant *E. coli* UGT73 and UGT73AH1 in a reaction.
Figure 4B:
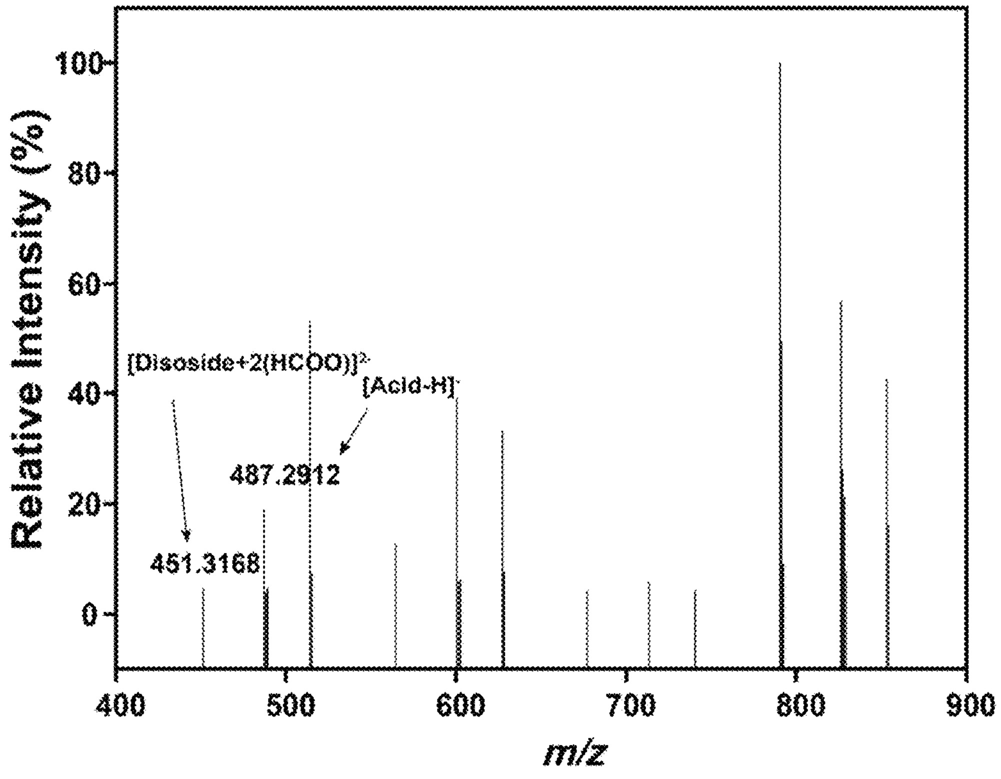
FIG. 4B shows mass spectrograms on negative ion fragments of crude enzyme solutions of recombinant *E. coli* UGT73 and UGT73AH1 in a reaction.
Figure 6A:
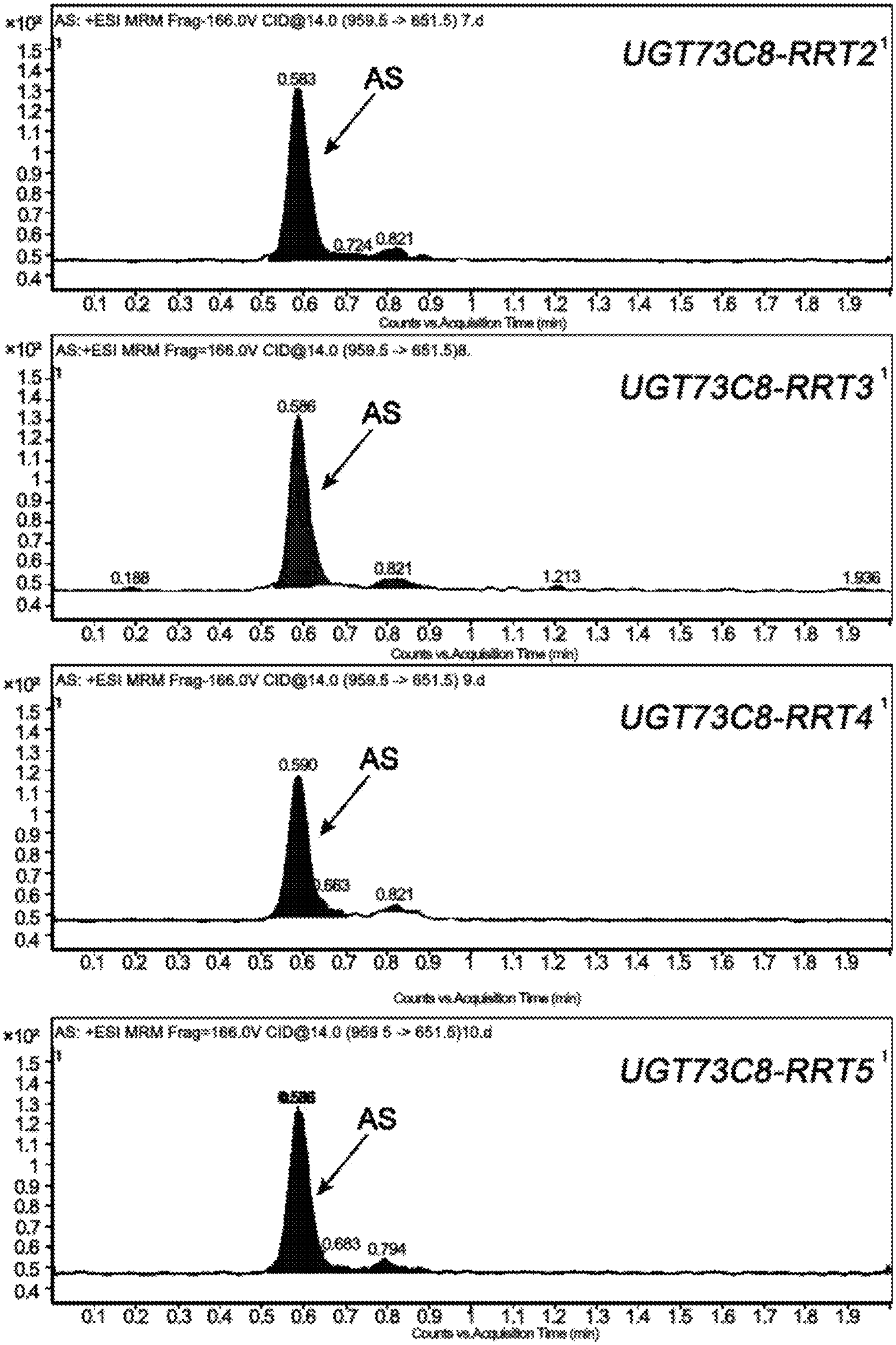
FIG. 6A-D shows liquid phase results of recombinant *E. coli* RRT and VvRHM in shake flask fermentation.
Figure 6B:
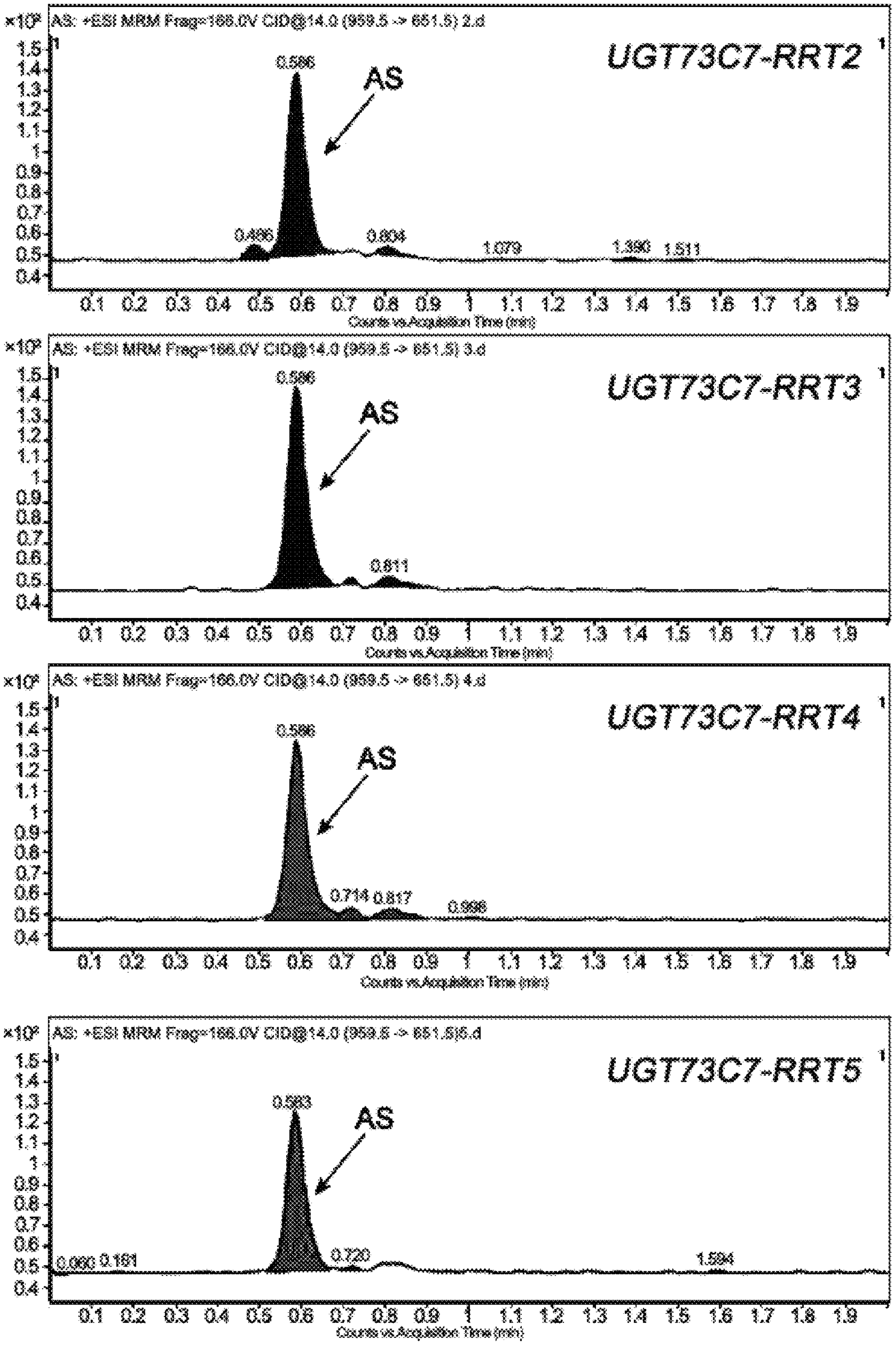
Figure 6C:
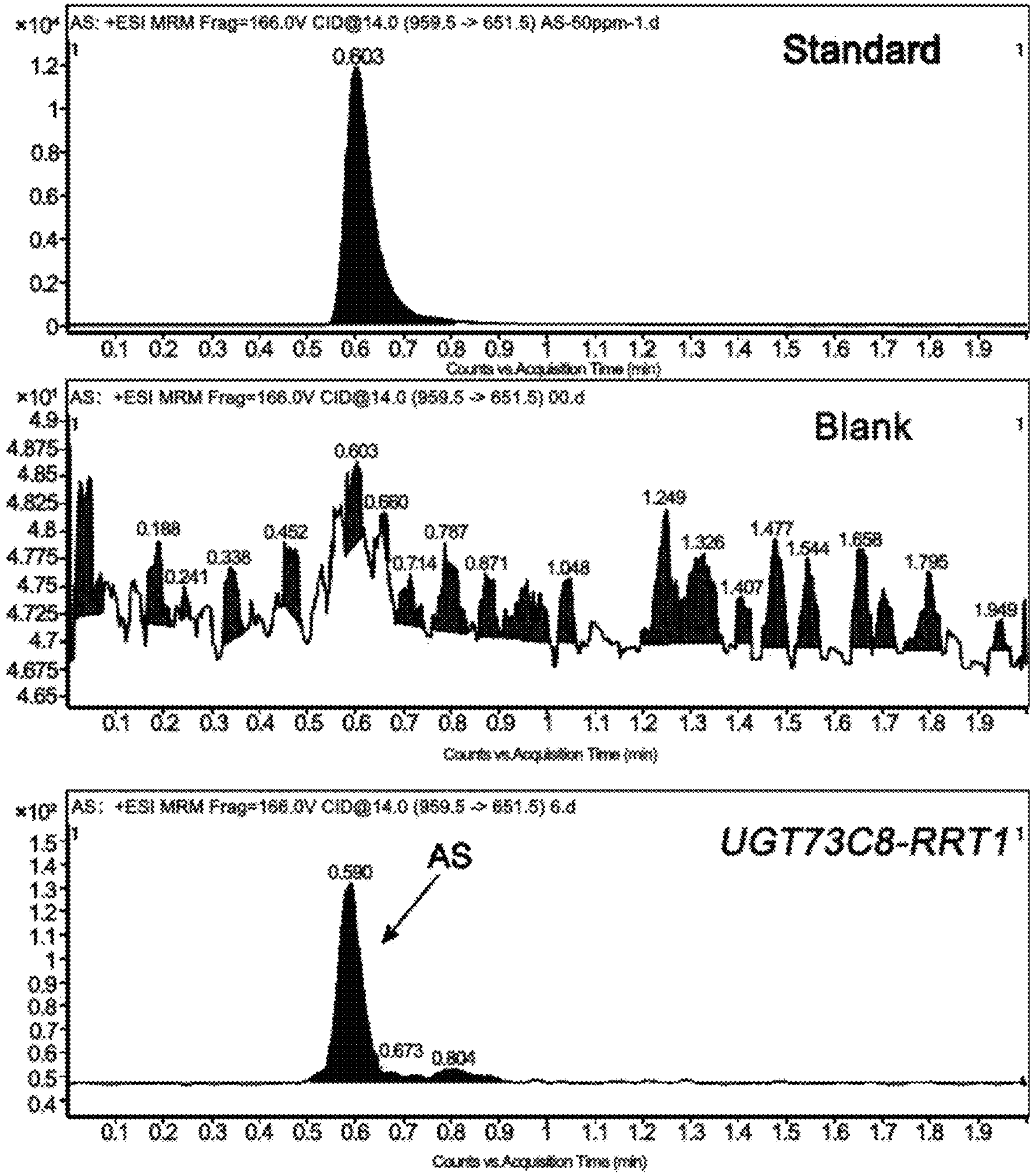
Figure 6D:
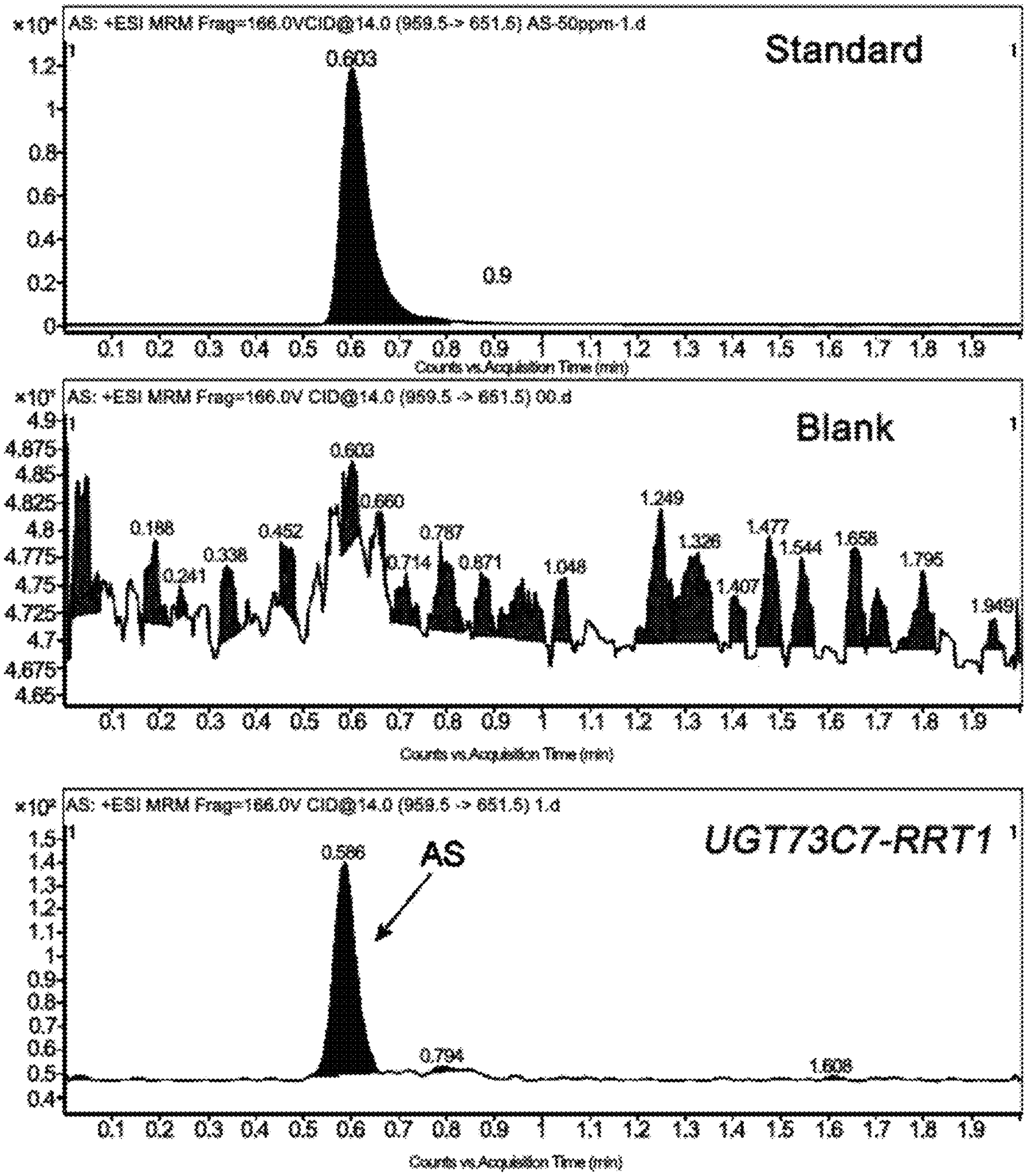
Figure 7:
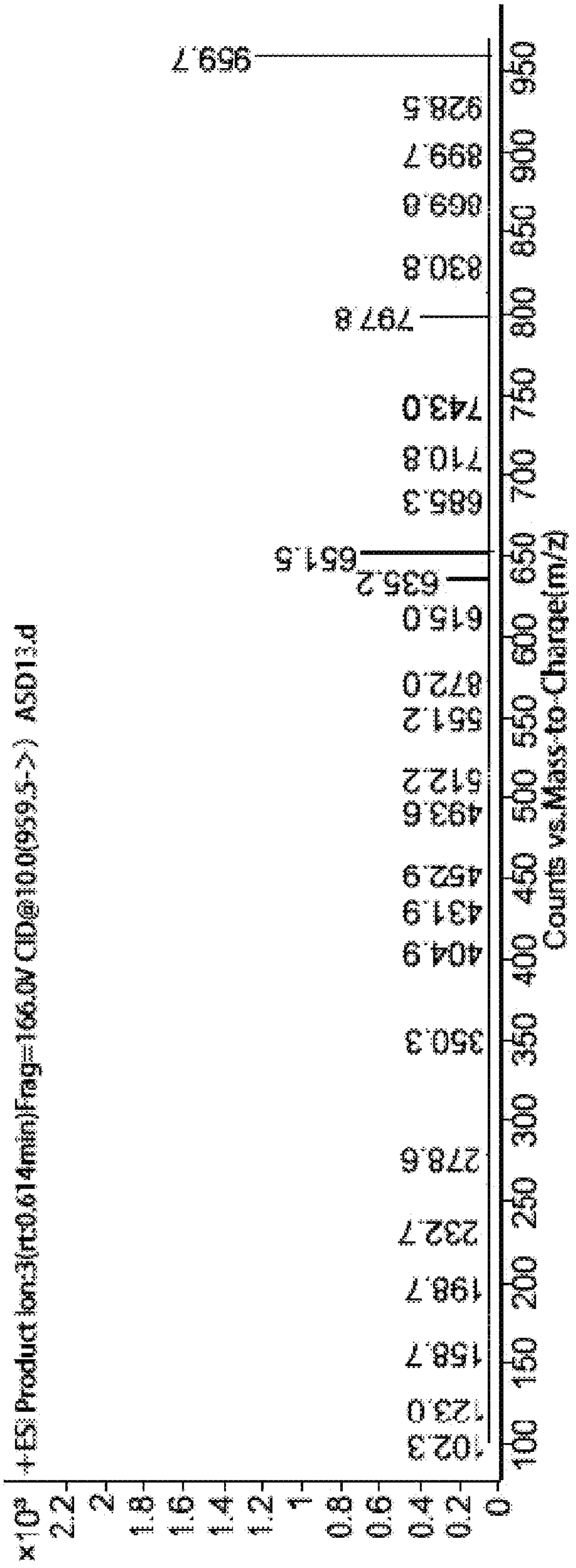
FIG. 7 shows mass spectrometry results of recombinant *E. coli* RRT and VvRHM in shake flask fermentation.

The volume of the total enzyme reaction system was 500 μl, the volume of the crude enzyme solution was 100 μl, the final concentration of the added UDPG was 1 g/L, the final concentration of asiatic acid added as a substrate was 200 mg/L, and the system was supplemented with a PBS buffer solution to 500 μl to carry out a reaction at 37° C. for 6 h. After completion of fermentation, an equal volume of methanol was added, violently shaken and uniformly mixed, followed by centrifugation at 14,000 r/min for 10 min. A supernatant was taken and filtered with a 0.22 μm organic phase filter membrane, and a product was detected by UPLC-IT-TOF/MS of Shimadzu. As can be seen from mass spectrograms in FIG. 4A and FIG. 4B, when UGT73AH1, UGT73C7 and UGT73C8 are transferred into the strain BL21 (DE3)Δpgi at the same time, a new peak different from that of the blank control appears at 7.92 min, and mass spectrum data same as that of asiaticodiglycoside are obtained, determining that asiaticodiglycoside is produced.

Example 6 Screening of Rhamnosyltransferases with Potential Functions

Through BLAST comparison between data of a transcriptome of *Centella asiatica* and rhamnosyltransferases that have known functions and are derived from 50 different sources in documents, results show that 5 isoenzymes are basically homologous to genes of the rhamnosyltransferases that have known functions in documents, and the E value is 0. Meanwhile, according to KEGG enrichment analysis, 5 rhamnosyltransferases in the transcriptome of *Centella asiatica* can be annotated.

TABLE 3

| Rhamnosyltransferases with high similarity | | | |
|---|---|---|---|
| Transcriptome gene ID | Number | Functional annotation of KEGG | Functional annotation of GO |
| evm.model.CM025780.1.1337[mRNA] | RRT1 | K23280 RRT; | ND |
| evm.model.CM025784.1.1860[mRNA] | RRT2 | rhamnogalacturonan I | |
| evm.model.CM025781.1.322 [mRNA] | RRT3 | rhamnosyltransferase | |
| evm.model.CM025784.1.718[mRNA] | RRT4 | [EC:2.4.1.351] | |
| evm.model.CM025785.1.2450[mRNA] | RRT5 | | |

Example 7 Gene Amplification of Glycosyltransferase and Construction of Recombinant *E. coli* for Expressing Rhamnosyltransferase With cDNA obtained by reverse transcription of *Centella asiatica* as a template, priming pairs (Table 4) used for amplifying sequences of the rhamnosyltransferases screened in Example 6 were designed and subjected to amplification by PCR, respectively by selecting a Primer Star MasterMix high-fidelity pfu enzyme (Takara) under the following conditions: pre-denaturation at 95° C. for 3 min; at an amplification stage, 30 cycles at 95° C. for 15 s, at 60° C. for 15 s and at 72° C. for 1 min; and extension at 72° C. for 5 min. PCR products were purified to obtain target fragments RRT1 to RRT5, meanwhile, a vector pRSFDuet-1 was subjected to amplification by PCR with a primer pair VvRHM-F and VvRHM-R, and a product was purified. The purified fragments RRT1 to RRT5 were recombined with the vector pRSFDuet-1 skeleton by a Gibson assembly method to obtain recombinant vectors, respectively, and the recombinant vectors were transferred into *E. coli* JM109. The vectors obtained were sent to Shanghai Biotech for sequencing to obtain correctly sequenced recombinant plasmids pRSFDuet-1-RRT1 to pRSFDuet-1-RRT5. Then, the plasmids were transferred into *E. coli* BL21 (DE3)Δpgi to obtain recombinant *E. coli* BL21 (DE3)Δpgi/pRSFDuet-1-RRT1 to BL21 (DE3)Δpgi/pRSFDuet-1-RRT5, respectively.

With a synthetic sequence as a template, a primer pair (Table 4) used for amplifying rhamnose isomerase VvRHM derived from *Vitis vinifera* was designed and subjected to amplification by PCR by selecting a Primer Star MasterMix high-fidelity pfu enzyme (Takara) under the following conditions: pre-denaturation at 95° C. for 3 min; at an amplification stage, 30 cycles at 95° C. for 15 s, at 56° C. for 15 s and at 72° C. for 1 min; and extension at 72° C. for 5 min. A PCR product was purified, a vector pRSFDuet-1 was subjected to amplification by PCR, and a product was purified. A purified fragment VvRHM and the vector pRSFDuet-1 skeleton were recombined by a Gibson assembly method to obtain a recombinant vector, and the recombinant vector was transferred into *E. coli* JM109. The obtained vector was sequenced by Shanghai Biotech, correctly compared and then transferred into *E. coli* BL21 (DE3)Δpgi to obtain recombinant *E. coli* BL21 (DE3)Δpgi/pRSFDuet-1-VvRHM.

TABLE 4

| Primers used for constructing expression vectors of glucosyltransferases | | |
|---|---|---|
| Primer | Sequence (5'-3') | |
| RRT1-F | TAATAAGGAGATATACCATGGAGGTTAGATCCGAGAGTGTACAGTTG AGG | SEQ ID NO: 52 |
| RRT1-R | GATTACTTTCTGTTCGATCATCTCGAAGTTTCTGTTGAATTGACGGTAC CTAATACG | SEQ ID NO: 53 |
| RRT2-F | TAATAAGGAGATATACCATGTGTGAATTAGATGAGAACAGGGAAGAG AGGGAGA | SEQ ID NO: 54 |
| RRT2-R | GATTACTTTCTGTTCGATCATGTAATTCTTAATGGTTCAACCAAGGGTT GCAAACACTC | SEQ ID NO: 55 |
| RRT3-F | ATAAGGAGATATACCATGGAGTTTAGATCTGAGAATGCACAGAATAG GTGTGATAAACTG | SEQ ID NO: 56 |
| RRT3-R | CGATTACTTTCTGTTCGATTACCGGAACTTCTCAGTTAAATTGCCCGGG | SEQ ID NO: 57 |
| RRT4-F | TAATAAGGAGATATACCATGGGGTGGAAGACATTAGGAGGTGAGAGT AG | SEQ ID NO: 58 |
| RRT4-R | TACTTTCTGTTCGATCAGATGATGCTTAGAAGTTCTTCAGATGAAACTT CTGAAAATCGC | SEQ ID NO: 59 |

TABLE 4-continued

| Primers used for constructing expression vectors of glucosyltransferases | | |
|---|---|---|
| Primer | Sequence (5'-3') | |
| RRT5-F | AATAAGGAGATATACCATGAAAAGTGTGAGAGTGGAGGGGAGAGGG | SEQ ID NO: 60 |
| RRT5-R | GATTACTTTCTGTTCGATCATTCAAGTGTATATTGTTCAACCAAGGGCTGAAAACAC | SEQ ID NO: 61 |
| VvRHM-F | tttaactttaataaggagatataccATGGCGACCCATACCCCG | SEQ ID NO: 62 |
| VvRHM-R | CATggtatatctccttTTACTCGAGCGCTTTCACTTCGG | SEQ ID NO: 63 |

Example 8 Induced Expression of Rhamosyltranserase

With a strain BL21 (DE3)Δpgi/pRSFDuet-1 transformed with an empty vector pRSFDuet-1 as a control, the series of recombinant *E. coli* constructed in Example 7 were subjected to streak culture on an LB plate containing kanamycin with a concentration of 50 μg/mL at 37° C. for 12 h, respectively. Single bacterial colonies were selected, transferred into 5 mL of an LB liquid culture medium containing kanamycin with a concentration of 50 μg/mL and subjected to shaking culture at 220 rpm at 37° C. for 12 h. The single bacterial colonies were transferred into 25 mL of a TB liquid culture medium containing kanamycin with a concentration of 50 μg/mL at an inoculation amount of 1% by volume and subjected to shaking culture at 220 rpm at 37° C. until an $OD_{600}$ value was 0.6-0.8. Isopropyl thiogalactoside (IPTG) was added to a final concentration of 0.5 μmol/L and subjected to shaking culture continuously at 220 rpm at 16° C. for 20 h.

After completion of culture, 1 mL of a bacterial solution was sucked to determine the final $OD_{600}$ value. 1 mL of the bacterial solution was centrifuged at 5,000×g for 1 min to collect bacteria, and the bacteria were resuspended with 1 mL of a 0.1 M PBS buffer solution with a pH value of 7.4, centrifuged at 5,000×g for 1 min and then washed to remove the residual culture medium. The bacteria were resuspended with a 0.1 M PBS buffer solution with a pH value of 7.4 to control the $OD_{600}$ value of a final resuspended bacterial solution at 5. The bacteria were crushed with an ultrasonic crusher. After completion of crushing, a crushed solution was collected and centrifuged at 12,000×g for 2 min, and a supernatant, namely, a crude enzyme solution of rhamnosyltransferase, was collected. SDS-PAGE results are shown in FIG. 5.

Example 9 Production of Asiaticoside by Induced Fermentation of Recombinant *E. coli*

(1) Construction of Recombinant *E. coli* for Producing Asiaticoside

Glucosyltransferase UGT73C7 with an amino acid sequence shown in SEQ ID NO: 13 was linked between XbaI and EcoRI restriction enzyme cutting sites of a vector pETDuet-1, glucosyltransferase UGT73AH1 with an amino acid sequence shown in SEQ ID NO: 19 was linked between NdeI and XhoI restriction enzyme cutting sites of the vector pETDuet-1 to construct a recombinant vector, and the recombinant vector was transferred into *E. coli* JM109. The obtained vector was sequenced by Shanghai Biotech to obtain a correctly sequenced recombinant plasmid pETDuet-1-UGT73AH1-UGT73C7.

Glucosyltransferase UGT73C8 with an amino acid sequence shown in SEQ ID NO: 14 was linked between XbaI and EcoRI restriction enzyme cutting sites of a vector pETDuet-1, glucosyltransferase UGT73AH1 with an amino acid sequence shown in SEQ ID NO: 19 was linked between NdeI and XhoI restriction enzyme cutting sites of the vector pETDuet-1 to construct a recombinant vector, and the recombinant vector was transferred into *E. coli* JM109. The obtained vector was sequenced by Shanghai Biotech to obtain a correctly sequenced recombinant plasmid pETDuet-1-UGT73AH1-UGT73C8.

The recombinant plasmid pETDuet-1-UGT73AH1-UGT73C7 or pETDuet-1-UGT73AH1-UGT73C8 was transferred into the series of recombinant *E. coli* constructed in Example 7 to obtain recombinant *E. coli* BL21 (DE3) Δpgi/pRSFDuet-1-RRT1/pETDuet-1-UGT73AH1-UGT73C7 to BL21 (DE3)Δpgi/pRSFDuet-1-RRT5/pETDuet-1-UGT73AH1-UGT73C7, BL21 (DE3)Δpgi/pRSFDuet-1-RRT1/pETDuet-1-UGT73AH1-UGT73C8 to BL21 (DE3)Δpgi/pRSFDuet-1-RRT5/pETDuet-1-UGT73AH1-UGT73C8, BL21 (DE3)Δpgi/pRSFDuet-1-VvRHM-RRT/pETDuet-1-UGT73AH1-UGT73C7, and BL21 (DE3)Δpgi/pRSFDuet-1-VvRHM-RRT/pETDuet-1-UGT73AH1-UGT73C8.

(2) Production of Asiaticoside by Shake Flask Fermentation

With a strain BL21 (DE3)Δpgi/pRSFDuet-1/pETDuet-1 transformed with empty vectors pRSFDuet-1 and pETDuet-1 as a control, the series of recombinant *E. coli* constructed in step (1) were subjected to streak culture on an LB plate containing kanamycin with a concentration of 50 μg/mL and ampicillin with a concentration of 50 μg/mL at 37° C. for 12 h, respectively. Single bacterial colonies were selected, transferred into 5 mL of an LB liquid culture medium containing kanamycin with a concentration of 50 μg/mL and ampicillin with a concentration of 50 μg/mL and subjected to shaking culture at 220 rpm at 37° C. for 12 h. The single bacterial colonies were transferred into 25 mL of a TB liquid culture medium containing kanamycin with a concentration of 50 μg/mL and ampicillin with a concentration of 50 μg/mL at an inoculation amount of 1% by volume and subjected to shaking culture at 220 rpm at 37° C. until an $OD_{600}$ value was 0.6-0.8. IPTG was added to a final concentration of 0.5 μmol/L, asiatic acid was added as a substrate after 6 h to reach a final concentration of 200 mg/L, shaking culture was performed continuously at 220 rpm at 30° C. for 48 h, and samples were collected and detected at 24 h.

After completion of fermentation, 2 ml of a fermentation solution was taken, added into an equal volume of methanol, violently shaken and uniformly mixed, followed by centrifugation at 14,000 r/min for 10 min. A supernatant was taken and filtered with a 0.22 μm organic phase filter membrane, and a product was detected by UPLC-IT-TOF/MS of Shimadzu. As can be seen from mass spectrograms in FIGS. 6A-D and FIG. 7, the UGT73AH1 and the glucosyltransferase (UGT73C7 or UGT73C8) undergo co-expression with the 5 rhamnosyltransferases screened in Example 6 to prepare asiaticoside by fermentation, respectively, and a unique new peak appears at 0.596 min, which is consistent with a characteristic ion flow of an asiaticoside standard product, determining that the substance is asiaticoside.

Although the present disclosure has been disclosed as above through exemplary examples, the examples are not intended to limit the present disclosure. For any person familiar with the art, various changes and modifications can be made without departing from the spirit and scope of the present disclosure. Therefore, the protection scope of the present disclosure should be as defined in the claims.

What is claimed is:

1. A recombinant *Escherichia coli*, comprising:

a glucosyltransferase gene encoding the peptide sequence SEQ ID NO: 13, and a glycosyltransferase UGT73AHI gene, wherein the recombinant *E. coli* expresses both the glucosyltransferase gene and the glycosyltransferase gene.

2. The recombinant *E. coli* according to claim 1, wherein the recombinant *E. coli* comprises a genome, and wherein a pgi gene of the genome is knocked out.

3. The recombinant *E. coli* according to claim 2, wherein the pgi gene has the nucleotide sequence set forth in SEQ ID NO:18.

4. The recombinant *E. coli* according to claim 2, wherein the glycosyltransferase UGT73AH1 gene is a *Centella asiatica* (L.) Urban glycosyltransferase UGT73AH1.

5. The recombinant *E. coli* according to claim 1, wherein the recombinant *E. coli* is *E. coli* BL21 (DE3) is used as a host.

6. A method for producing asiaticodiglycoside, which comprises:

(a) inoculating a seed liquid of the recombinant *E. coli* according to claim 1 into a fermentation culture medium, (b) shaking the fermentation culture medium until an $OD_{600}$ value is 0.6 from 0.6 to 0.8, (c) adding isopropyl thiogalactoside, (d) adding asiatic acid to a final concentration of 150 mg/L to 250 mg/L after 4 hours to 8 hours, and (e) shaking the fermentation culture medium continuously for 40 hours to 60 hours.

7. The method according to claim 6, wherein the fermentation culture medium comprises:

15-25 g/L of glucose, 4-6 g/L of glycerol, 14-18 g/L of $K_2HPO_4 \cdot 3H_2O$, 1-3 g/L of $KH_2PO_4$, 20-30 g/L of yeast powder, and 10-15 g/L of peptone.

8. The recombinant *E. coli* of claim 1, wherein the recombinant *E. coli* further comprises an expression vector, and wherein the glucosyltransferase gene and the glycosyltransferase gene are both encoded on the expression vector.

9. The recombinant *E. coli* of claim 8, wherein the expression vector expresses both the glucosyltransferase gene and the glycosyltransferase gene when induced to express.

10. The recombinant *E. coli* of claim 8, wherein the expression vector is a pETDuet-1 vector.

11. The recombinant *E. coli* of claim 1, wherein the glycosyltransferase UGT73AH1 gene comprises the amino acid sequence set forth in SEQ ID NO: 19.

12. A composition, comprising:

(i) the recombinant *E. coli* of claim 1, and (ii) asiatic acid and/or asiaticodiglycoside.

* * * * *

SEQUENCE LISTING

```
Sequence total quantity: 69
SEQ ID NO: 1            moltype = DNA  length = 2739
FEATURE                 Location/Qualifiers
source                  1..2739
                        mol_type = other DNA
                        organism = synthetic construct
SEQUENCE: 1
atgaccagca gtcagctgaa agaactgcat tttattttca tcccgctgct gagtccgggt  60
catgttatgc cgatggttga tattgcacgt ctgtttgccc agcatggtat taccgtgacc  120
attattagca ccccgctgaa taccgcacgt tttaaaacca ttgtggatcg tgcagtggtg  180
gaaagcggtc tgcgtattca gattgttgat ctggattttc cggccgccga agccggttta  240
ccggaaggtt gtcagaatat ggatagcatt agtcgtgata tgatcaccaa tttcttcacc  300
gccagcagta tgctgcagca gccgttagaa gatattctgg aaaatctgag tccgcgtccg  360
agctgtatta ttagtggtaa aaatctggcg tggaccgtgg aaaccgccct gaaattcaaa  420
attccgcgcc tgtttttcga tggtaccggt tgttttagtt tcgcctgtgc aaatcatctg  480
cagaatagtg aagaattctg gcgtgttagt agtaaaaccg aaccggtgct ggtgccgggc  540
ttagcacatg atattgttct gaccaaagca cagctgccgg aagcactgaa tccgcatggt  600
agtggcgatc tgcatgcagt tcgtgaaaaa atggttaatg cagaaagcat cgccgatggc  660
attattgtta atagtttcga agagctggag ccggattatg ttaaagatta taagcgtgtg  720
aagggcggca atgtttggtg tattggtccg gtgagcgcat gcaataagct gaatattgat  780
aaggccgaac gtggtaatct ggattgcgca aaaggtaccc attgcctgga atggctggat  840
agccaggaac cgaatagtac cattcatgca tgtctgggta gtattagcgg tctgaccgcc  900
agccagctgg tggagttagc actgggtctg gaagccagta aacgtccgtt tatttgggtt  960
attcgtagtg gtaaacgcag tgaagaactg gaaaaatgga ttgaagagga aaacttcgag  1020
gcccgtacca aaggtcgtgg tctgctgatt cgtggttggg cccctcagct gctgattctg  1080
gctcatagca gcattggtgg ttttctgacc cattgtggtt ggaatagtac catcgaaggt  1140
ctgagtgccg gtaaaccgat tattacctgt ccgctgtttg ccgaacagtt tattaatgaa  1200
aagctggttg tggaggtgct gggtaccggt gttagcgtgg gtgtggaagc cgcagttgca  1260
tggggtctgg aagataaaag tggcctggtt atgaaacgcg aaaatgtgaa aaaggccatt  1320
gaaaaagtgc tggataaggg taaagagggc gaagaacgtc gcgaacgtgc acgtgaaatt  1380
ggcgaaatgg cccgcatggc cattgaagaa ggtggtagca gctattttaa catgaaaagc  1440
ctgatccagt acgttatgga acagaatgaa ctgaatcacg gcagtattgg catgctgaaa  1500
gaacagtttg aaacctttgt gcaggatatt aagccgccgg caaattgtat tattagcgat  1560
agctgcttcc cgtggaccac cgaaattagt ctgaaatttc atatcccgcg tatcgttttt  1620
aacggcccgt gttgttttag cctgctgagc agttataata tcttcaccag ccgcgttctg  1680
gatgaagttg ttagtgatag tgaaaccttc gtggtgccgg gcctgaatga tcgtgtggaa  1740
ctgaccaaaa gtaaactggc cggtatgatt aatccgcgtg tgaatagcgt tatgaaagat  1800
ctgtttgagc agattatgga gagcgaagca gccagctttg gtattgtggc aaataccttt  1860
gaagagctgg aaaccgtgtg tcagcgtgtg cataaaggta gtctgagtca gctgccgacc  1920
agtcagatga ttgaactggg cctgggcctg gaagaaagca aacgcccttt tatttggtgc  1980
attcgccatg aaaccgaaga atttggcaaa tggattagta aggagggtta tggtgaacgc  2040
accaaaggtc gcggtctgct gatccgtggt tgggcacctc aggttctgat tctgagccat  2100
caggccattg gtggctttct gacccgttgc ggctggaata gcaccctgga aggcattagc  2160
gcaggtgaac agctgctgac ctggcctttc tttgcagaac agtttatcaa tgaggagttc  2220
gtggttaaaa tcatccgtac cggtatgcgc attggcgtgg aacatccgat tgtttttggt  2280
gacgaagaac gcgttggcgt gctggcaaaa cgcgatgcaa ttaagaatgc cattgaaatg  2340
ctgatgaacg aagaagaaga ggcacaggaa cgccgcaaac gcgcaagaga actgggtgaa  2400
atggcaagca aagccaccga agaaggtggc agcagctatt tcaatatgac catgctgatt  2460
caggacatta tccagcagca tagcaaaggc cgtagcgcag cacatgtgag cgaaaaattt  2520
cgtaaatgtc agggtttcac cggcctgatt attctggcac tgccgtatcg tcattgtaat  2580
gaagttgtgt atcgcaaaga gatcaagctg gaactgcatg aagtttttcg ttttgatgag  2640
gtggatcatg cactggcaaa agttagcgtt gttattagcg aatgcgtgcc gggttggatt  2700
tgggccgaag atattgtggg tccgctgctg aataagtaa                         2739

SEQ ID NO: 2            moltype = DNA  length = 729
FEATURE                 Location/Qualifiers
source                  1..729
                        mol_type = other DNA
                        organism = synthetic construct
SEQUENCE: 2
atggatgatc tctcttctct aaaactgggt gttaaatttt ttcaagcaaa tgaaatgctt  60
caagaaccac tagaaaaact gatgggagaa ctggtgccaa ggccgagctg catcgtttca  120
actagtgctc tgccgtggac taatgaggtt gcttggaaat tcaacatcct aagagacaga  180
atggagaaac cgaggcccac tgaacatcca gctcgagttt ctttgtgcaa caaacgtctt  240
tcagacatgt cgaatagaga acttggttta gggctagaag cctcaaatca tccctttatg  300
```

-continued tggataatcc gaaagagtga ctattcacca caattagaga aatggttgga ggaatatggg 360
tttgaagaga gggtgaaagg aagaggccta attatccatg gttgggcgcc acaagttctg 420
atactttcgc atccctctgt tggaggattt ttaactcatt gcggatggaa ttcaactcta 480
gaagcagttt gcgcgggcat gccaatgatc acttggcctg tgtttggtga gcagttttac 540
aatgaaaact tcgtggtcaa tatactacag attggtgtcc gagttggggt tgatgttgga 600
ttgggatcta gggggaagtg gagtgttaca gtgaaggaat ctgcagaaaa tgaaagcttg 660
aagaatggac acgtcggcaa gttggttaca cttaaatgtg gaagtccgcc gtttgttaag 720
ggaaagtaa 729

SEQ ID NO: 3 moltype = DNA length = 1488
FEATURE Location/Qualifiers
source 1..1488
mol_type = other DNA
organism = synthetic construct
SEQUENCE: 3
atggctacca atattgagca gcagcagcag cagcttcact ttgtgatggt tcctcttatg 60
tcccaaagcc atatcattcc cttgacagat tttgccaaac tacttgcgca acgaggacaa 120
attgtgacca taatctcaac tcccctcaat gccatccgtt acaaacccat cattgatcga 180
gccaagatga acaacctcaa tatccaacta gttgctctcc agtttccgac ccgcgaggct 240
ggattgcccg aagggtgtga aaacatggat gaactctctt ctctgaagtt tggttttaat 300
tttttcgaag cgaatgaaat gctccgggat ccactagaaa aagtgatggg agaactggtg 360
ccaaggccta gctgcatcgt atcaacaact gctctgccgt ggactaatga ggttgcttgg 420
aaattcaaca ttcctaggta tggtttcaat actatttcat gcttcagtct agtatgttct 480
aacaagatta agatttccaa ggtgcatgaa agtctcacct cggattcaga ttcatttgtc 540
gtcccggatt taccagacaa aattgagatt aaaaggtccc agttaccgga atatacgatg 600
aaaaaaaactt caaacaatga gggaaaaaac atacttgaca aaatgaaacc cacggagcat 660
cccgcacgag ggctgttagt gaatactttt gaggagatgg agccatctta tgttgaagaa 720
tacaggaaac aggaaagtag agtttggtgc attgggtctg tttctttgtc caacaaagat 780
gtttcagata tgtcgaatag aggtaacaag gcctccattg aagaagaaga ttgcttgaaa 840
tggcttgatt caatgaagcc atgttctgtc atttatgttt gttttgggag cctttctaat 900
atcccatcct ctcaattgat agaacttggt ttggggctag aagcctcgaa ttgccccttc 960
atttggataa tccgaaagcg cgactattca ccacaagtag agaaatggct agaagaatac 1020
aggtttgaag agagggtgaa aggaagaggc ctaattatcc tcggttgggc gccacaagta 1080
ctaatacttt cccatccctc tgttggagga ttcttcactc attgtgggtg gaattcaact 1140
ctagaaggag tttgcgcggg cgtgccgatg atcacttggc ctatgtttgc tgagcagttt 1200
tacaatgaaa agtttgtggt caatgtacta aggactggtg tccgagttgg ggttgatgtt 1260
ggattgggat ctagagagga cgacaactcc caaatcctgg tgaagagtga acaagtgaag 1320
gaggtcatag atcagttgat ggatggtgag gaggcagagg aaagaagaca gagagctcgg 1380
caacttaaag aaaaagcaaa taaggctatt gaaggaggag gatcttctta tttgaacatt 1440
actatgttca ttgaagatgt caggcaacaa aatttaagtc attcatga 1488

SEQ ID NO: 4 moltype = DNA length = 1506
FEATURE Location/Qualifiers
source 1..1506
mol_type = other DNA
organism = synthetic construct
SEQUENCE: 4
atggattcac aatttcagca gcttcacttt gttatgatac ccttaatgtg tcctggccac 60
cttattccac tggtggacat ggccaaattg cttgctcaac gggccgtcac cgtcaccatt 120
gtcaccactc cccgaaacgc catccgtttc ggggcagcca cttctcgggc aatccaatcc 180
gggctgccca ttcggctcct ggaactccgg tttccaacgc tggaggccgg attgcccgaa 240
ggttgcgaaa acgttgacca actctcctct tttgacttct ccaaaaaactt tattgatgcg 300
tcaaaaatgc aacaaggtcc attagaaaaa atatttggag acataaagcc tagcccaagc 360
tgcataattt cggacaagca tatcatgtgg accgctaaaa ctgctaagaa atttcaaatt 420
ccatggattg tgtttgatgg aatgagctgt ttcaatcagt tgtgtacaga gatattacac 480
actacaaaag tacacgaaaa cgtgtccgag tcggaaccct ttgttgtccc tggtttgcct 540
gatgttattg agttcaagag agcccaactc cccggattgt ttaatccggg gagcaatcca 600
ggttcagcga atgtaaatga tattcgcgaa caaataaggg caactgaagt tggagcttat 660
ggggttgtga tcaatagttt tgaagagttg gaacacgatt atgttagaga atttaagaag 720
attaaagaag gtaaagtttg gtgtgtaggt ccattatcat tatgcaatac tgatgacata 780
gataaggctc agagaggaaa caatgtagcc atggatcaac agcataaatg tttacaatgg 840
cttgatgcag agaaaaatgg ttctgtaata tatgtttgtc ttggaagcct aagcagcctt 900
agtaacctca gtggtgcaca gattatagag cttgctttag gcttggaaat gtctggatat 960
ccatttatat gggcgctgag gcctgggatt aaacataaag agattgagaa atgggtgata 1020
gaagaagggt ttgaagaaag agttaaaggc agaggaatgt tgatctgggg ttgggcacca 1080
caagtgctta tattgtcaca ccgcgctatt gggggattct tgacacattg tggatggaat 1140
tcgacaattg aagggatatg tgctggtgtt ccgatgatca catggccttt gttcgcggag 1200
cagtttgtta atgagaagtt tttagtgcag gttgtgaaga ctggtgtgag agttggggtt 1260
gaggctgttg tggatatggg ttataaagaa gagtttgggg tgaaagtgaa gagggaggat 1320
gttaaaaatg ctgtagagtg catcatgtct gaagatgagg aaggggaata tagaaggaac 1380
agagccaaga agcttgcaga gatggctgtg aaagcagttg aagagggtgg ctcttctaat 1440
cttaatatga cattgctgat tcaagacatc attgaacaag taaaggatag gttagcatta 1500
agctaa 1506

SEQ ID NO: 5 moltype = DNA length = 1488
FEATURE Location/Qualifiers
source 1..1488
mol_type = other DNA
organism = synthetic construct

```
SEQUENCE: 5
atgggttcag aatctcaagt gcagcttcac tttgtcatga tacccttaat gtgtccaggc  60
caccttattc cactggtaga catggccaaa ttgctagcac aactggccgt gaccgtcact  120
attgttacca ctccccggaa tgccatccgt tttggtgcag ccacggctcg tgccattgca  180
tctggcctct ccattaggct tcttgaactc aggtttccgg cagtggaggc cggattgcca  240
gatgggtgcg aaagcgtaga tgatctcccc tcttttgacc tgacagcaaa ttttttttgtg  300
gcaacaaaaa tgatgcaaaa gccactagag aacatgttcc aagacattaa gccaagtcca  360
agctgcataa tctcggacaa gcttgtggtt tggacttctg aaactgctaa aaagtttaac  420
attccttgga ttatatttga tggaatgagc tgttttacac agttgtgtac agatagaata  480
cacacttcaa aagttcatga gactgtatcc gagacagaat tctttgttgt cccagatttg  540
cctgatgtta ttgaattcaa gaaagcccaa ctgcccggat tgttcaattc agggaacaat  600
ccaggttcag taaatatgaa aaatcgagaa gagattagag cagctgaaat aggagcttat  660
ggggttgtta tcaacagttt tgaagagttg gaacatgctt atgtgaagga atttaagaag  720
atcagcggaa ataaagtttg gtgtataggc ccattgtcat tatgcaataa tgatgacatg  780
gataaggctc agagaggaaa caatatcatc actgatcatc acctcaaatg cttacaatgg  840
cttgatactc aaagaactga ctctgtaata tatgcttgtc tcggaagcct aagcagcctt  900
agtaacctca gttgcgagca gattattgag cttgctttag gcttagaagc ttcggggcat  960
ccatttatat gggcgctgag ggtggggagt aaacacgaaa agatagagaa atggatatca  1020
gaagaggggt ttgaagaaag aattgaaggc aggggaattc tgatccgcgg ttgggcgcca  1080
caagtactta tattgtcaca cactgcaata ggaggattct tgacacattg cggatggaat  1140
tcaacagttg aagggatctg cgctggcgta ccaatgatca catggccttt gttcgcggag  1200
cagtttttta atgagaagtt tttggtgcaa gtggtggaga ctggtgtgag aattggggtt  1260
gatgtaattg tgacaatggt tgaggaggaa agggttgggg tgaaagtgaa gagtggggat  1320
gttaaaaagg ccatagagcg cataatgtgt ggaggagaag aaggggaaaa tagaaggaaa  1380
agagccaagg agcttgcaaa gatggctgtg gaggcagtgg aagagggagg atcttcttac  1440
cttaatatga cgttactaat ccaagacatt ttgaaagaaa ggaagtga              1488

SEQ ID NO: 6           moltype = DNA  length = 1482
FEATURE                Location/Qualifiers
source                 1..1482
                       mol_type = other DNA
                       organism = synthetic construct
SEQUENCE: 6
atggccaact tagctcaaaa ccttcatttt gtcttgcttc ctttcatggc tcaaggccat  60
atcattccta tggtggacat agccaaattg cttgcgcgac gcggcacaat tgttaccatc  120
atcagcacac ctgttaatgc cacccggttc aaagcaactg tcactcgctc agtacaatcg  180
ggccttcaaa tccgcatggt tgaactctat tttccaagtg aggaagtagg actgccaaaa  240
gggtgtgaaa atatagacat gttgggggca tcaaatttgt ctggaaattt ttttgaagca  300
acttttatgc tccgagaagc tgtagaaaat ttttcttagag atgcaaatcc atccccaagt  360
tgcataatct ccgatatgtg tttcccatgg acaactgatg ttgctcaaaa gtttcacatt  420
ccacgactta ttttccatgg accatcttgt ttttctctct tgtctatgca tcttcttcat  480
acttccaagg ttcttgatag actagctccg gattctgaga aacttgtatt gcctggccta  540
cccgacagaa ttgaaatggc tacggctacg tttgtaggtt tgatcaaacc ttcgggctca  600
attcaagatt cgtctcccat gaaagacttt tttgataaga ttattgagtc cgaaaaggca  660
tcattcgggg tagtggctaa tacttttgaa gagttggagc cagagtatgt caaagagttt  720
gtaagagtaa agggtactaa actttggagt attggacctg tttcattgtg caacaaagac  780
aacgatgaaa aggtcgagag aggtaacaaa acttcgatta atgaagacga gtgcttgaaa  840
tggctcgatt cacatgaacc aggctcagtg gtgtatgttt gtttgggaag cttatcaaag  900
ctagcaactt cccaattgat agaacttggg ttgggactag aagcatcgaa tgtaccattt  960
atttggtgta taagaagaga aacagaagga tttaggacgt gggctttgca agaaaatttt  1020
gaagaaagaa tcaaagggag aggccttttg atcaaggggt gggcacccca agttttgata  1080
ctgtcacacc aagctgttgg aggatttcta acacattgtg ggtggaactc gacgttggag  1140
ggaatttgtg ctggcattca aatgctgaca tggcctttgt ttgctgacca gttccttaat  1200
gaggctttag tagtgcagat tctaaggaca ggaatgaagg tgggtgtgga gagtcctgtc  1260
atttttggag aagaagagag tgttggagtg ttgatagaaa gagatgctgt taaattggct  1320
atagacaggc tcatgaatca tgaagatgag gggaaggaga gaaggaaaag agttaaagaa  1380
cttggggaaa tggctaaaag agcaatggag gaagatggtt cttcttacct taacatgaca  1440
cacctaattc aagaaattat ggcccatggg acaagtaaat ga                    1482

SEQ ID NO: 7           moltype = DNA  length = 1527
FEATURE                Location/Qualifiers
source                 1..1527
                       mol_type = other DNA
                       organism = synthetic construct
SEQUENCE: 7
atgtcccgaa tcagcggtcc gccaaaccca gtgtcccaaa ttgattgtcc accaatgtca  60
ttgactcaaa aacttcactt tgtcctagtc ccattactgg ctcaaggcca catgatccca  120
atgattgaca tggccaggct gctagcgcaa catggcgtcg tggtaagtct ggtcaccacc  180
cctctcaacg ccttgagatt tgcgacagca attcatcgcg caaggacttc tgggcttaaa  240
attcagctca tagaaatccc attcccctgg caagaagtgg ggcttccatc aggatatgaa  300
aatcttgaca gccttccttc gagggacctc ataggaaaat tttatagtgc acttcatatg  360
ttgcaacagc cactagaaca acatcttcaa cagcaaatgc cacctccaag ctgcataatt  420
tcggacaaat gtctttcctg gacatctgag attgccaaaa agtttgaggt tccaagactg  480
gtttttcatg ggatgtgctg tttttcacta ctaagttcac ataatgttag gcttcataat  540
gctcacttgt ctgtcacttc agactctcaa ccttttgtgg ttccggggat gccccaaagg  600
gttgaaataa caaaagccca gttgccagga gcatttgtta aacttccgga tttggacgat  660
attcgtgaca gaatgcgtga ggctgaatca agtgcttatg gagttgtggt taacagtttc  720
actgagttgg aaaatgggtg tgcgaaaagg tacaaaaagg ccatcggtaa aaaggtttgg  780
tgcattggac cagtgtcact ctgtaataaa gaaaatctgg acaagtttga gagaggaaac  840
```

aaggcctcaa ttgatgagaa gagctgcaca gagtggcttg attccatgaa accaaagtct 900
gtgatctatg cttgtttggg cagtcaatgc cggctcgttc cagcacagct gatggaactt 960
gggttggcac tggaatcatc aaaccaacct ttcatctggg taatcaaaga aggagaaaga 1020
tttcaagaaa tggagaaatg gttagtagag cagaagtttg aggagagaat caaagggaga 1080
ggacttttga tcaaggggtg ggcaccacag gttcttatac tttcacatcc agcaatcaag 1140
gctttttga cacattgtgg ttggaactca accattgaag gagtttgttt tggtgtccca 1200
atgataacat ggcctatgtt tgcagagcag ttcttcaatg aaaaacttat agtggatatt 1260
cttaagattg gtgtcaaagt tggggttcaa ttctctgtta gatgggggga ggaagagaaa 1320
gttggtgttg tggttaaaaa agggcaaatt gagaaagcta tagaaaagat tatgaatggg 1380
ggaggtgaag gagaaagtat aaagattaga gcaagaaacc tttcagaaat aggaaggcag 1440
gccatggaag atggagggtc ctctcactcc aacatgtcac agttgattca agatatccgg 1500
aaattgaaca atcaagaaaa tgtttga 1527

SEQ ID NO: 8 moltype = DNA length = 1392
FEATURE Location/Qualifiers
source 1..1392
mol_type = other DNA
organism = synthetic construct
SEQUENCE: 8
atgggaacta ttgcaaacgg agaaattgcc cgaaaacctc acattatgtt aatcgctttt 60
ccggcgcaag gtcacatgag cccaatgatg caattcgcca agcgtctagc ttccaaaggc 120
acgcgtgtca ctgtcgtggc tgccgccatc ggcattgtca gaagtagtat cgaagaagac 180
acaacgagct ccatcaactt tgagtacatt tcttacaaat ttgaagatga tgaaatacca 240
gacggtgcta aatcctacat gggctacatg aaactcaaag tcctcaaaag tttgcctgga 300
cttgttgaaa aacaaaaatt ttatgggcac cctgtggaag tcctattgta tgattcgctt 360
cttccatggg gattagattt gtgtcgagaa cttggagtac gaggaggtcc acttttcact 420
caaagttgtg ctgtttgtgc catttactgg cacactcatc tggggagcct gaggctcccc 480
gttgagggtc tcacaacggt atccctgtct gcgatgccgt tgatggcaat taatgatttg 540
ccttcgtccg tgtatgacgg tttgtatccg ggattgttgg agattcttag gaaccagttc 600
gttaatttgg agaaagcgga ttggatattc ttcaacactt ttgacaagct tgaagatgag 660
gtagcagaat ggttgtcaag ccagtggcct attaagacta tcggaccatc aattccatca 720
atgttcttag acaaacgatt agctgatgac aaagattacg gcctcagcct cttcaagcca 780
gatgttgaag cttgcatcaa gtggttagat gctaaagatg ttggctctgt agtctatgta 840
tcttttggca gcttcgtaga ccttggccaa gaatatatga gcgaactcgc gtggggtttg 900
ttaaacagca acaatttctt tttatgggta gttagagaat ctgaacagat taagcttcca 960
agtaatttct gtacagaagc cgcggagaaa ggcctagtag tgagttggtg cccgcagctc 1020
gaagttttgg ctcataagtc tgtggggagt ttcatgacac attgcgggtg gaactcaaca 1080
atcgaagcat tgagcttagg agtgccaatg ctggtaatgc ctcaatggac ggatcaaacg 1140
acgaatgcta aatttattgt ggatgtttgg caaactggag ttcgagttaa ggatattgac 1200
aaggagagtg ttacaaggga agatattgca gattgcataa aggaggtcat gaatggaaca 1260
aaaggggaag agcttaaaac aaatgctgtc aaatggaagg agctggcagt agaggcaatg 1320
agtgaaggtg ggagctctga caagaatatc gacgaattca tttcagaaat tagatcaatt 1380
accacttgtt ga 1392

SEQ ID NO: 9 moltype = DNA length = 1506
FEATURE Location/Qualifiers
source 1..1506
mol_type = other DNA
organism = synthetic construct
SEQUENCE: 9
atggattctc aatttcaaca attgcatttt gttatgattc cattaatgtg tccaggtcac 60
ttaattccat tagttgatat ggctaaatta ttagcacaaa gagctgttac tgttactatt 120
gttactactc ctagaaatgc tattaggttt ggtgcagcta cttctagagc aattcaatct 180
ggtttaccaa ttagattatt agaattgaga tttccaactt tagaagctgg tttacctgaa 240
ggttgtgaaa atgttgatca attgtcatct tttgattttt ctaaaaattt tattgatgca 300
tctaaaatgc aacaaggtcc attagaaaag atttttggag atataaaacc atctccttca 360
tgtataatta gtgataaaca tattatgtgg acagctaaaa ctgctaaaaa atttcaaatt 420
ccatggattg tttttgatgg tatgtcatgt tttaatcaat tatgtactga aattttacat 480
acaactaaag ttcatgaaaa tgtgtctgaa tcagaacctt ttgttgttcc aggtttacca 540
gatgttattg agtttaaaag agctcaatta ccaggtttat tcaatcctgg tagtaatcct 600
ggttctgcta atgttaatga cattagagaa caaattagag ctacagaagt tggtgcatac 660
ggtgttgtta ttaatagttt tgaagaattg gaacatgact atgttagaga attcaagaaa 720
attaaggaag gtaaagtttg gtgtgttggt ccattaagtt tgtgtaatac tgatgatatt 780
gataaagctc aaagaggtaa taatgttgct atggatcaac aacataaatg tttacaatgg 840
ttagatgctg aaaagaatgg ttcagtaatc tatgtttgtt tgggtagttt atcttcattg 900
tctaacttat caggtgctca aattattgaa ttggcattag gtttagaaat gagtggttac 960
ccattcattt gggccttgag accaggtata aaacataaag aaatagaaaa atgggttatt 1020
gaagaaggtt ttgaagaaag agttaaaggt agaggtatgt tgatttgggg ttgggctcct 1080
caagtcttaa ttttatctca tagagctata ggtggatttt taactcattg tggttggaat 1140
tcaactattg aaggaatttg tgcaggtgtt ccaatgatta catggccatt gtttgctgaa 1200
caatttgtta atgaaaaatt tttggttcaa gttgtaaaaa caggtgttag agttggtgtt 1260
gaagcagttg ttgatatggg ttataaagaa gaatttggtg ttaaagttaa acgtgaagat 1320
gttaaaaatg cagttgaatg tataatgagt gaagatgaag aaggtgaata tagaagaaat 1380
agagctaaaa aattagctga aatggctgtt aaagctgttg aagaaggtgg ttctagtaat 1440
ttgaatatga ctttattaat tcaagatata attgaacaag ttaaagatag attagctttg 1500
tcttaa 1506

SEQ ID NO: 10 moltype = AA length = 912
FEATURE Location/Qualifiers

```
source                  1..912
                        mol_type = protein
                        organism = synthetic construct
SEQUENCE: 10
MTSSQLKELH FIFIPLLSPG HVMPMVDIAR LFAQHGITVT IISTPLNTAR FKTIVDRAVV  60
ESGLRIQIVD LDFPAAEAGL PEGCQNMDSI SRDMITNFFT ASSMLQQPLE DILENLSPRP  120
SCIISGKNLA WTVETALKFK IPRLFFDGTG CFSFACANHL QNSEEFWRVS SKTEPVLVPG  180
LAHDIVLTKA QLPEALNPHG SGDLHAVREK MVNAESIADG IIVNSFEELE PDYVKDYKRV  240
KGGNVWCIGP VSACNKLNID KAERGNLDCA KGTHCLEWLD SQEPNSTIHA CLGSISGLTA  300
SQLVELALGL EASKRPFIWV IRSGKRSEEL EKWIEEENFE ARTKGRGLLI RGWAPQLLIL  360
AHSSIGGFLT HCGWNSTIEG LSAGKPIITC PLFAEQFINE KLVVEVLGTG VSVGVEAAVA  420
WGLEDKSGLV MKRENVKKAI EKVLDKGKEG EERRERAREI GEMARMAIEE GGSSYFNMKS  480
LIQYVMEQNE LNHGSIGMLK EQFETFVQDI KPPANCIISD SCFPWTTEIS LKFHIPRIVF  540
NGPCCFSLLS SYNIFTSRVL DEVVSDSETF VVPGLNDRVE LTKSKLAGMI NPRVNSVMKD  600
LFEQIMESEA ASFGIVANTF EELETVCQRV HKGSLSQLPT SQMIELGLGL EESKRPFIWC  660
IRHETEEFGK WISKEGYGER TKGRGLLIRG WAPQVLILSH QAIGGFLTRC GWNSTLEGIS  720
AGEQLLTWPF FAEQFINEEF VVKIIRTGMR IGVEHPIVFG DEERVGVLAK RDAIKNAIEM  780
LMNEEEEAQE RRKRARELGE MASKATEEGG SSYFNMTMLI QDIIQQHSKG RSAAHVSEKF  840
RKCQGFTGLI ILALPYRHCN EVVYRKEIKL ELHEVFRFDE VDHALAKVSV VISECVPGWI  900
WAEDIVGPLL NK                                                     912

SEQ ID NO: 11           moltype = AA  length = 242
FEATURE                 Location/Qualifiers
source                  1..242
                        mol_type = protein
                        organism = synthetic construct
SEQUENCE: 11
MDDLSSLKLG VKFFQANEML QEPLEKLMGE LVPRPSCIVS TSALPWTNEV AWKFNILRDR  60
MEKPRPTEHP ARVSLCNKRL SDMSNRELGL GLEASNHPFM WIIRKSDYSP QLEKWLEEYG  120
FEERVKGRGL IIHGWAPQVL ILSHPSVGGF LTHCGWNSTL EAVCAGMPMI TWPVFGEQFY  180
NENFVVNILQ IGVRVGVDVG LGSRGKWSVT VKESAENESL KNGHVGKLVT LKCGSPPFVK  240
GK                                                                242

SEQ ID NO: 12           moltype = AA  length = 495
FEATURE                 Location/Qualifiers
source                  1..495
                        mol_type = protein
                        organism = synthetic construct
SEQUENCE: 12
MATNIEQQQQ QLHFVMVPLM SQSHIIPLTD FAKLLAQRGQ IVTIISTPLN AIRYKPIIDR  60
AKMNNLNIQL VALQFPTREA GLPEGCENMD ELSSLKFGFN FFEANEMLRD PLEKVMGELV  120
PRPSCIVSTT ALPWTNEVAW KFNIPRYGFN TISCFSLVCS NKIKISKVHE SLTSDSDSFV  180
VPDLPDKIEI KRSQLPEYTM KKTSNNEGKN ILDKMKPTEH PARGLLVNTF EEMEPSYVEE  240
YRKQESRVWC IGSVSLSNKD VSDMSNRGNK ASIEEEDCLK WLDSMKPCSV IYVCFGSLSN  300
IPSSQLIELG LGLEASNCPF IWIIRKRDYS PQVEKWLEEY RFEERVKGRG LIILGWAPQV  360
LILSHPSVGG FFTHCGWNST LEGVCAGVPM ITWPMFAEQF YNEKFVVNVL RTGVRVGVDV  420
GLGSREDDNS QILVKSEQVK EVIDQLMDGE EAEERRQRAR QLKEKANKAI EGGGSSYLNI  480
TMFIEDVRQQ NLSHS                                                  495

SEQ ID NO: 13           moltype = AA  length = 501
FEATURE                 Location/Qualifiers
source                  1..501
                        mol_type = protein
                        organism = synthetic construct
SEQUENCE: 13
MDSQFQQLHF VMIPLMCPGH LIPLVDMAKL LAQRAVTVTI VTTPRNAIRF GAATSRAIQS  60
GLPIRLLELR FPTLEAGLPE GCENVDQLSS FDFSKNFIDA SKMQQGPLEK IFGDIKPSPS  120
CIISDKHIMW TAKTAKKFQI PWIVFDGMSC FNQLCTEILH TTKVHENVSE SEPFVVPGLP  180
DVIEFKRAQL PGLFNPGSNP GSANVNDIRE QIRATEVGAY GVVINSFEEL EHDYVREFKK  240
IKEGKVWCVG PLSLCNTDDI DKAQRGNNVA MDQQHKCLQW LDAEKNGSVI YVCLGSLSSL  300
SNLSGAQIIE LALGLEMSGY PFIWALRPGI KHKEIEKWVI EEGFEERVKG RGMLIWGWAP  360
QVLILSHRAI GGFLTHCGWN STIEGICAGV PMITWPLFAE QFVNEKFLVQ VVKTGVRVGV  420
EAVVDMGYKE EFGVKVKRED VKNAVECIMS EDEEGEYRRN RAKKLAEMAV KAVEEGGSSN  480
LNMTLLIQDI IEQVKDRLAL S                                           501

SEQ ID NO: 14           moltype = AA  length = 495
FEATURE                 Location/Qualifiers
source                  1..495
                        mol_type = protein
                        organism = synthetic construct
SEQUENCE: 14
MGSESQVQLH FVMIPLMCPG HLIPLVDMAK LLAQLAVTVT IVTTPRNAIR FGAATARAIA  60
SGLSIRLLEL RFPAVEAGLP DGCESVDDLP SFDLTANFFV ATKMMQKPLE NMFQDIKPSP  120
SCIISDKLVV WTSETAKKFN IPWIIFDGMS CFTQLCTDRI HTSKVHETVS ETEFFVVPDL  180
PDVIEFKKAQ LPGLFNSGNN PGSVNMKNRE EIRAAEIGAY GVVINSFEEL EHAYVKEFKK  240
ISGNKVWCIG PLSLCNNDDM DKAQRGNNII TDHHLKCLQW LDTQRTDSVI YACLGSLSSL  300
SNLSCEQIIE LALGLEASGH PFIWALRVGS KHEKIEKWIS EEGFEERIEG RGILIRGWAP  360
QVLILSHTAI GGFLTHCGWN STVEGICAGV PMITWPLFAE QFFNEKFLVQ VVETGVRIGV  420
DVIVTMVEEE RVGVKVKSGD VKKAIERIMC GGEEGENRRK RAKELAKMAV EAVEEGGSSY  480
```

```
LNMTLLIQDI LKERK                                                495

SEQ ID NO: 15          moltype = AA  length = 493
FEATURE                Location/Qualifiers
source                 1..493
                       mol_type = protein
                       organism = synthetic construct
SEQUENCE: 15
MANLAQNLHF VLLPFMAQGH IIPMVDIAKL LARRGTIVTI ISTPVNATRF KATVTRSVQS  60
GLQIRMVELY FPSEEVGLPK GCENIDMLGA SNLSGNFFEA TFMLREAVEN FLRDANPSPS  120
CIISDMCFPW TTDVAQKFHI PRLIFHGPSC FSLLSMHLLH TSKVLDRLAP DSEKLVLPGL  180
PDRIEMATAT FVGLIKPSGS IQDSSPMKDF FDKIIESEKA SFGVVANTFE ELEPEYVKEF  240
VRVKGTKLWS IGPVSLCNKD NDEKVERGNK TSINEDECLK WLDSHEPGSV VYVCLGSLSK  300
LATSQLIELG LGLEASNVPF IWCIRRETEG FRTWALQENF EERIKGRGLL IKGWAPQVLI  360
LSHQAVGGFL THCGWNSTLE GICAGIQMLT WPLFADQFLN EALVVQILRT GMKVGVESPV  420
IFGEEESVGV LIERDAVKLA IDRLMNHEDE GKERRKRVKE LGEMAKRAME EDGSSYLNMT  480
HLIQEIMAHG TSK                                                  493

SEQ ID NO: 16          moltype = AA  length = 508
FEATURE                Location/Qualifiers
source                 1..508
                       mol_type = protein
                       organism = synthetic construct
SEQUENCE: 16
MSRISGPPNP VSQIDCPPMS LTQKLHFVLV PLLAQGHMIP MIDMARLLAQ HGVVVSLVTT  60
PLNALRFATA IHRARTSGLK IQLIEIPFPW QEVGLPSGYE NLDSLPSRDL IGKFYSALHM  120
LQQPLEQHLQ QQMPPPSCII SDKCLSWTSE IAKKFEVPRL VFHGMCCFSL LSSHNVRLHN  180
AHLSVTSDSQ PFVVPGMPQR VEITKAQLPG AFVKLPDLDD IRDRMREAES SAYGVVVNSF  240
TELENGCAKR YKKAIGKKVW CIGPVSLCNK ENLDKFERGN KASIDEKSCT EWLDSMKPKS  300
VIYACLGSQC RLVPAQLMEL GLALESSNQP FIWVIKEGER FQEMEKWLVE QKFEERIKGR  360
GLLIKGWAPQ VLILSHPAIK AFLTHCGWNS TIEGVCFGVP MITWPMFAEQ FFNEKLIVDI  420
LKIGVKVGVQ FSVRWGEEEK VGVVVKKGQI EKAIEKIMNG GGEGESIKIR ARNLSEIGRQ  480
AMEDGGSSHS NMSQLIQDIR KLNNQENV                                  508

SEQ ID NO: 17          moltype = AA  length = 463
FEATURE                Location/Qualifiers
source                 1..463
                       mol_type = protein
                       organism = synthetic construct
SEQUENCE: 17
MGTIANGEIA RKPHIMLIAF PAQGHMSPMM QFAKRLASKG TRVTVVAAAI GIVRSSIEED  60
TTSSINFEYI SYKFEDDEIP DGAKSYMGYM KLKVLKSLPG LVEKQKFYGH PVEVLLYDSL  120
LPWGLDLCRE LGVRGGPLFT QSCAVCAIYW HTHLGSLRLP VEGLTTVSLS AMPLMAINDL  180
PSSVYDGLYP GLLEILRNQF VNLEKADWIF FNTFDKLEDE VAEWLSSQWP IKTIGPSIPS  240
MFLDKRLADD KDYGLSLFKP DVEACIKWLD AKDVGSVVYV SFGSFVDLGQ EYMSELAWGL  300
LNSNNFFLWV VRESEQIKLP SNFCTEAAEK GLVVSWCPQL EVLAHKSVGS FMTHCGWNST  360
IEALSLGVPM LVMPQWTDQT TNAKFIVDVW QTGVRVKDID KESVTREDIA DCIKEVMNGT  420
KGEELKTNAV KWKELAVEAM SEGGSSDKNI DEFISEIRSI TTC                 463

SEQ ID NO: 18          moltype = DNA  length = 1650
FEATURE                Location/Qualifiers
source                 1..1650
                       mol_type = other DNA
                       organism = synthetic construct
SEQUENCE: 18
atgaaaaaca tcaatccaac gcagaccgct gcctggcagg cactacagaa acacttcgat  60
gaaatgaaag acgttacgat cgccgatctt tttgctaaag acggcgatcg tttttctaag  120
ttctccgcaa ccttcgacga tcagatgctg gtggattact ccaaaaaccg catcactgaa  180
gagacgctgg cgaaattaca ggatctggcg aaagagtgcg atctggcggg cgcgattaag  240
tcgatgttct ctggcgagaa gatcaaccgc actgaaaacc gcgccgtgct gcacgtagcg  300
ctgcgtaacc gtagcaatac cccgattttg gttgatggca aagacgtaat gccggaagtc  360
aacgcggtgc tggagaagat gaaaaccttc tcagaagcga ttatttccgg tgagtggaaa  420
ggttataccg gcaaagcaat cactgacgta gtgaacatcg ggatcggcgg ttctgacctc  480
ggcccataca tggtgaccga agctctgcgt ccgtacaaaa accacctgaa catgcacttt  540
gtttctaacg tcgatgggac tcacatcgcg gaagtgctga aaaaagtaaa cccggaaacc  600
acgctgttct tggtagcatc taaaaccttc accactcagg aaactatgac caacgcccat  660
agcgcgcgtg actggttcct gaaagcggca ggtgatgaaa aacacgttgc aaaacacttt  720
gcggcgcttt ccaccaatgc caaagccgtt ggcgagtttg gtattgatac tgccaacatg  780
ttcgagttct gggactgggt tggcggccgt tactctttgt ggtcagcgat tggcctgtcg  840
attgttctct ccatcggctt tgataacttc gttgaactgc tttccggcgc acacgcgatg  900
gacaagcatt tctccaccac gcctgccgag aaaaacctgc ctgtactgct ggcgctgatt  960
ggcatctggt acaacaattt ctttggtgcg gaaactgaag cgattctgcc gtatgaccag  1020
tatatgcacc gtttcgcggc gtacttccag cagggcaata tggagtccaa cggtaagtat  1080
gttgaccgta acggtaacgt tgtggattac cagactggcc cgattatctg gggtgaacca  1140
ggcactaacg gtcagcacgc gttctaccag ctgatccacc agggaaccaa aatggtaccg  1200
tgcgatttca tcgctccggc tatcacccat aacccgctct ctgatcatca ccagaaactg  1260
ctgtctaact tcttcgccca gaccgaagcg ctggcgtttg gtaaatcccg cgaagtggtt  1320
gagcaggaat atcgtgatca gggtaaagat ccggcaacgc ttgactacgt ggtgccgttc  1380
aaagtattcg aaggtaaccg cccgaccaac tccatcctgc tgcgtgaaat cactccgttc  1440
```

```
agcctgggtg cgttgattgc gctgtatgag cacaaaatct ttactcaggg cgtgatcctg  1500
aacatcttca ccttcgacca gtggggcgtg gaactgggta aacagctggc gaaccgtatt  1560
ctgccagagc tgaaagatga taaagaaatc agcagccacg atagctcgac caatggtctg  1620
attaaccgct ataaagcgtg gcgcggttaa                                    1650

SEQ ID NO: 19          moltype = AA  length = 501
FEATURE                Location/Qualifiers
source                 1..501
                       mol_type = protein
                       organism = synthetic construct
SEQUENCE: 19
MDSQFQQLHF VMIPLMCPGH LIPLVDMAKL LAQRAVTVTI VTTPRNAIRF GAATSRAIQS  60
GLPIRLLELR FPTLEAGLPE GCENVDQLSS FDFSKNFIDA SKMQQGPLEK IFGDIKPSPS  120
CIISDKHIMW TAKTAKKFQI PWIVFDGMSC FNQLCTEILH TTKVHENVSE SEPFVVPGLP  180
DVIEFKRAQL PGLFNPGSNP GSANVNDIRE QIRATEVGAY GVVINSFEEL EHDYVREFKK  240
IKEGKVWCVG PLSLCNTDDI DKAQRGNNVA MDQQHKCLQW LDAEKNGSVI YVCLGSLSSL  300
SNLSGAQIIE LALGLEMSGY PFIWALRPGI KHKEIEKWVI EEGFEERVKG RGMLIWGWAP  360
QVLILSHRAI GGFLTHCGWN STIEGICAGV PMITWPLFAE QFVNEKFLVQ VVKTGVRVGV  420
EAVVDMGYKE EFGVKVKRED VKNAVECIMS EDEEGEYRRN RAKKLAEMAV KAVEEGGSSN  480
LNMTLLIQDI IEQVKDRLAL S                                             501

SEQ ID NO: 20          moltype = DNA  length = 1497
FEATURE                Location/Qualifiers
source                 1..1497
                       mol_type = other DNA
                       organism = synthetic construct
SEQUENCE: 20
atggaggtta gatccgagag tgtacagttg aggtgtgata agctgattcc cagaactaga  60
tttcaagtgt ggttcattag gatttgtttc agcattttga tatggacctg tttggttcag  120
ctagttgcag ttggtgagtt gtggcatcca tatttgttaa gtgggttatc ggatcgttca  180
aatgggtctt ctaagctatt tataaacagg aatgcagttc cgtccttgcc tccacttcct  240
ccggcaagga actacacgag taatggtttt ctcagggttt cttgcaatgg gggtttaaat  300
caaatgcgtg ctgcgatctg tgacatggtt gcagtttctc gactcttgaa ccttactttg  360
gttgttccag agcttgataa gacatcattc tgggcagatc ctagtgattt tgaggacatt  420
tttgatgtga gacacttcat tgattcattg agagatgaag ttcgaattgt caaaaggtta  480
ccaaaaaggt ttatccaaag atatggatac aggccattag aaatgcctcc ggtcagctgg  540
tccagtgaaa aatactatct gcaacagatt ctgcctcttt ttgacaagca taagttgata  600
catttcaaca gaacagatac acggttggca aacaatatga ttccccttga tcttcagaaa  660
ttcaggtgtc gcgtaaattt tcgggcactg agattcactc ctcaaattga ggctttggga  720
cagaaattgg ttcatatact tgaagggaaa ggatcattta tagcattaca tctcagatac  780
gaaatggata tgttggcttt ctcgggttgt acacatggat gcacagagga agaagctgaa  840
gagctgaaac gattgaggta tgcatttcct tggtggaggg agaaagagat agtgtctgga  900
gaaaggagat cacaaggtct gtgccctctt accoctgagg aggcagcttt agtgctgcgg  960
gcactagata ttgacaataa cacccagata tatattgcat ctggtgagat ttatggcagc  1020
gaaaagagac ttgctgtgtt aaaggctgca tttccacgga ttgtgaagaa ggaaatgctg  1080
ctagatgctg atgatttgcg acaattccaa aatcattcat cccaaatggc agctctggac  1140
ttcatggtat ctgttgccag caatgttttc attcccactt atgacggtaa catggcaaag  1200
cttgtggaag gtcatcgcag atattttggg tttaaaaaga ccatccaact agatcggcga  1260
agaattgtgc aattgattga tttacatcag aacgggacac ttgcatggga tgagttctca  1320
gctgctatta gattgacaca tgaaggaagg acaggacagc ccacacgtcg tagagttgat  1380
gcagaaaaac ccaaagaaga agactacttc tatgcgaacc cttatgagtg tttttgcgag  1440
ggaacaagtt gtggtaacgt attaggtacc gtcaattcaa cagaaacttc gagatga      1497

SEQ ID NO: 21          moltype = DNA  length = 1530
FEATURE                Location/Qualifiers
source                 1..1530
                       mol_type = other DNA
                       organism = synthetic construct
SEQUENCE: 21
atgtgtgaat tagatgagaa cagggaagag agggagaaac agtggaagat tggtatgaag  60
tttgtgggtg aaattaaaga ggaaagacaa agtttgatgg tttctcatgc tcgaaagttg  120
ttgtggattg tccgaggaat gacaacagtg ttgctttgga cttttgttat tcgattgttg  180
acaatgggtg agatttgggg tccaaggttg ttgaagagtt ggccgtcatg ttttaatcct  240
cctccaaata tgttaactga ggctaagatg tcttacattc atcccaaagt ttttcatcct  300
cctaagaggg tttacaagaa caatggttat cttatggttt cttgcaatgg aggcctcaat  360
caaatgagag gagcaatatg tgacatggtt gctattgcaa gatacctgaa tgtcactctt  420
attgttccag aactggataa agcctcattt tgggcagatc caagcgagtt tcaggacata  480
tttgatgttg atcatttcat aacatctttg agggatgagg ttcggatttt gaaagagctg  540
ccaccacggc tcaagagaag agttgagctt ggactgttct actcattgcc gcctattagt  600
tggtctgaca tttcctacta ccaaaaccag attcttcctc tacttcaaaa gtacaaagtc  660
gtgcatttaa atagaactga tgctcgactt gctaataatg ggttaccgct agagattcag  720
aaattgcgct gcaaagttaa ttttagtgct ctgagattca tgtcccaaat agaggagcta  780
ggtagaaaga ttgtcagcat cttgagggaa aatggccctt ttgttgtcct ccatcttagg  840
tatgagatgg atatgttggc tttctctggc tgcagtcatg gctgcaacag tgaagaggtc  900
aatgaattaa caagaatgag atatgcttac ccctggtgga aggaaaaaat tattgattcg  960
gaccttaaaa ggaaagaagg tttgtgtcct ttgacacctg aagaaactgc tctaatatta  1020
acagctttgg gtattgatca tgatgttcaa atttatattg ctgctggaga aatttatggt  1080
ggaggacgga gactagcaag cttggcagct gcctttccaa atttggtcaa aaaggagaaa  1140
ttgctggatc cttcagattt gaagtacttt cagaaccact cctcccaaat ggctgcacta  1200
```

-continued

```
gattatctcg tctccttgga gagtgacata tttgtgccta catatgatgg aaacatggct  1260
aaagttgttg agggtcatcg tagatattta ggatacaaga agactatctc attggacaga  1320
aagcttctag ttgatttgat agaccgtcac tatgctgggt cactaagctg ggacgagttt  1380
gcttcaacag tgaaggaaac acatgcagat agaatgggta gtgcaagaga acgactagtg  1440
atcccagaca gaccgaagga agaagactat ttctttgcca atccacacga gtgtttgcaa  1500
cccttggttg aaccattaag aattacatga                                   1530

SEQ ID NO: 22          moltype = DNA  length = 1509
FEATURE                Location/Qualifiers
source                 1..1509
                       mol_type = other DNA
                       organism = synthetic construct
SEQUENCE: 22
atggagttta gatctgagaa tgcacagaat aggtgtgata aactgcccgg gcaggtgatt  60
ccgaagacta ggttacaaat atggttcatt agggtttgtt ccagcatttt gatatggact  120
tgtttagttc agctagttac ggttggcgag ctttggcatc cacggttgct ggcagggcta  180
tccaatcgtt caaatggctc ttccaagatt tcaacagagg aaagggcggt tccgtcgctg  240
cttcctcttc ttcctgcaag gaactacact agtaatggtt ttctcaaagt ttcttgcaat  300
ggaggtttga atcaaatgcg tgctgcgatc tgtgacatgg ttacagttgc tcgactatta  360
aatcttactt tggttgttcc agagctggat aagacatcct tctgggctga tcctagtaat  420
ttcgaggata tttttaatgt gagacacttc attgattcat tgagagatga agttcacatt  480
gtcaaaagga ttccaaaaaa atttatcagg agatatggat accagtcact acaaatgcct  540
cctgttagct ggtcgagtga aaaatactac ctggaacaga tactgccact tttaacacag  600
cataagttga tacatttcaa cagaacagat acacggttgg caaacaatat gatccccctt  660
gatcttcaga aactcaggtg ccgtgtcaat ttccaggcac tgagattcac ccctcagatt  720
gaggctttgg gacagaaatt ggttgatatt cttcaaggga aaggaccatt tatagcattg  780
catctaagat atgagatgga tatgctggct ttctcaggtt gtacacatgg ctgcacagag  840
gaagaagctg taaagctaaa acgcttgagg tatgcatttc cttggtggag ggagaaagag  900
atagtgtctg aagagaggag atcactaggt ctatgccctc ttactccaga ggaggcagtt  960
ttagtgctgc aagcattaaa ttttgacaag gacacacaaa tatatattgc ctctggagag  1020
atttatggca gtgaaaggag acttgcagtt ctacgggctt catttccacg gattgtgaag  1080
aaagaaatgt tgctagatcc cggggaattg caacaatttc aaaatcattc atcccaaatg  1140
gctgccctgg acttcattgt ttccgtcgct agtagtgttt tcattcccac atatgatggc  1200
aacatggcaa agcttgtgga aggtcaccgc aggtatcttg ggttcagaaa gaccctccaa  1260
ctagaccgaa gaaaaattgt agaattaatc gactcatatc agaacaagac actttcatgg  1320
gaggatttcg tgggtgccat gagattgaca catgagagaa gaacaggaca gcccacaggt  1380
cgtaaagtca ttgcagacaa gcccaaagaa gaagattatt tttatgcaaa ccctcacgag  1440
tgcctctgtg aaagtccaaa ttgtgacaat ttacaacccc cgggcaattt aactgagaag  1500
ttccggtaa                                                         1509

SEQ ID NO: 23          moltype = DNA  length = 1500
FEATURE                Location/Qualifiers
source                 1..1500
                       mol_type = other DNA
                       organism = synthetic construct
SEQUENCE: 23
atggggtgga agacattagg aggtgagagt agaaaaagga ttgagaagtt aaggagttca  60
atggtttcta ggtctagaat gaagctgtgg atgattagag ctactacttc attgttgttg  120
tggacatgtg ttgttcagtt gacagctttg ggagagctgt gggggcctag ggttttgaag  180
ggttggcctt cttgttttac tcaggattct gtcatggata ttaagatgac tccagctctt  240
ccagctagag ttcttccacc caagagggtt tataagaaca atggttattt aatggtttca  300
tgcaatggag ggcttaatca gatgcgggct gcgatatgcg acatggttgc tattgcaaga  360
tatttaaatg ttacacttat agttcctgag ctggataaaa catctttttg ggctgatcca  420
agcgagttcc aagacatttt tgatgttgac catttcattt cgtccttgag agatgaggtt  480
cgtatactga aagagcttcc tcccaggatt aagaggagag tggaactagg aatgttctat  540
acaatggcac ccgtcagttg gtctgacatc tcttactatc ataatcagat tcttcctctg  600
gtacagaagt ataaagttgt gcatttgaat agaactgatg ctcgccttgc taacaatggc  660
cagccacttg agattcagaa gctccggtgc cgagtaaact ttggagctct gagatttact  720
cctcagatag aggagttggg aaggagggta gtcaagcttc taaggcagaa tggtcctttt  780
ctagtacttc atctcagata tgaaatggac atgctagcat tttcaggctg tagtcagggt  840
tgcaacaatg aagaggtgga tgagttgacg cggatgagat atgcataccc atggtggaaa  900
gagaagatca taaactctga tttgaaaaga aaggatggtc tatgtccgtt gacccctgaa  960
gaaactgctc tcacactaag ggcgctggac attgatcatg acatacagat ttacattgct  1020
gcaggagaaa tatatggcgg agagaggaga atggctagtc ttgctgccgc ttatccgaaa  1080
ctggttagga aggagactct tctgagtcag tcagaccttg gatattttaa gaatcactct  1140
tctcagatgg cagcattaga ttatcttgtt tcgttggaga gtgatatttt tgttcctaca  1200
tatgacggaa acatggccaa agttgttgaa ggtcatcgga gattccttgg gttgaagaag  1260
acaatactat tggacagaaa gctattagtt gatttgatag accaatataa tcatgggtca  1320
ctgaattggg atgaattctc tattgctgtt aagaacgctc atgcagaccg catgggaaat  1380
gccaccaaaa gattagtgat tccagacaga cctaaagaag aggactattt ctatgcgaat  1440
ccagaagagt gcttgcgatt ttcagaagtt tcatctgaag aacttctaag catcatctga  1500

SEQ ID NO: 24          moltype = DNA  length = 1506
FEATURE                Location/Qualifiers
source                 1..1506
                       mol_type = other DNA
                       organism = synthetic construct
SEQUENCE: 24
atgaaaagtg tgagagtgga ggggagaggg agaaaagaga gttggagtat gaagtttgtg  60
```

```
gatgagaaga aagaggcaaa atcaaggttt atggtttctc ggtctcgaat gatgttgtgg  120
attatcagag gaatgacgac tttgttgctt tggacatttg ttattcgatt attgacaatg  180
ggtgaagttt ggggtccaag gttgttgaag agttggcctt catgtatgtt tactgaggtc  240
aacctgtctg atgctcagcc caaggttttt cagcctccca agagggttta taagaacaat  300
ggctatcttt tggtttcttg caatggagga ctcaatcaaa tgcgaggagc catttgtgac  360
atggttgctg ttgcaagaca tctgaatgtc acacttattg tgccagaact ggataaaact  420
tcattttggg cagatccaag tgagtttaag gacatatttg atgttgatca ttttattgca  480
tccttgagag atgaggtgcg aattttgaag gaactgccac cacggcttaa gagaagagtt  540
gagcttggac tatatcactc attgccgcct attagttggt cggacatttc ctactatcat  600
aatcagattc ttccactact acaaaaatat aaagttgttc atttaaatag aaccgatgct  660
cgacttgcta acaatgggtt acctctggag atacagaagc tgcgttgcag agtaaatttt  720
agtgctctga aattcacttc tcaaatagaa accctaggta ggaaggtagt cagcatcttg  780
aggcaaaatg gccctttttgt cgtcctccat ctaagatatg aaatggatat gttggctttc  840
tccggctgca gccacggctg caacaacgaa gaggtggaac acctaacacg aatgagatat  900
gcttatccct ggtggaagga aaaggttata gattcagact tcaaaaggcg agaaggttta  960
tgccctctga cacctgaaga aactgctcaa gtattaactg cattgggcat caatcgcgat  1020
gttcaaatat atatagctgc tggagaaatt tatggtggag ctcgcagaat ggcaagtttg  1080
gctgctgcat ttccaaattt ggtcagaaag gagaacctgt tggatccttc agatttgagg  1140
tatttccaga accactcatc ccaaatggct gcactagatt atcttgtgtc cttgcagagt  1200
gacatatttg taccaacata tgatggaaac atggctaaag ttgttgaagg tcatcgcaga  1260
tacttaggat tcaagaagac catctcattg aacagaaagc ttctagtaga tttgattgat  1320
cgttatcatg gcggattgtt aagctgggat gacttctctt ccatggtgaa ggaatctcat  1380
gcagatcgga tggggagtgc caaacagcga ttagtaatcc cagatagacc aaaggaagaa  1440
gactatttct atgccaatcc acatgagtgt tttcagccct tggttgaaca atatacactt  1500
gaatga                                                            1506

SEQ ID NO: 25          moltype = AA  length = 498
FEATURE                Location/Qualifiers
source                 1..498
                       mol_type = protein
                       organism = synthetic construct
SEQUENCE: 25
MEVRSESVQL RCDKLIPRTR FQVWFIRICF SILIWTCLVQ LVAVGELWHP YLLSGLSDRS  60
NGSSKLFINR NAVPSLPPLP PARNYTSNGF LRVSCNGGLN QMRAAICDMV AVSRLLNLTL  120
VVPELDKTSF WADPSDFEDI FDVRHFIDSL RDEVRIVKRL PKRFIQRYGY RPLEMPPVSW  180
SSEKYYLQQI LPLFDKHKLI HFNRTDTRLA NNMIPLDLQK FRCRVNFRAL RFTPQIEALG  240
QKLVHILEGK GSFIALHLRY EMDMLAFSGC THGCTEEEAE ELKRLRYAFP WWREKEIVSG  300
ERRSQGLCPL TPEEAALVLR ALDIDNNTQI YIASGEIYGS EKRLAVLKAA FPRIVKKEML  360
LDADDLRQFQ NHSSQMAALD FMVSVASNVF IPTYDGNMAK LVEGHRRYFG FKKTIQLDRR  420
RIVQLIDLHQ NGTLAWDEFS AAIRLTHEGR TGQPTRRRVD AEKPKEEDYF YANPYECFCE  480
GTSCGNVLGT VNSTETSR                                               498

SEQ ID NO: 26          moltype = AA  length = 509
FEATURE                Location/Qualifiers
source                 1..509
                       mol_type = protein
                       organism = synthetic construct
SEQUENCE: 26
MCELDENREE REKQWKIGMK FVGEIKEERQ SLMVSHARKL LWIVRGMTTV LLWTFVIRLL  60
TMGEIWGPRL LKSWPSCFNP PPNMLTEAKM SYIHPKVFHP PKRVYKNNGY LMVSCNGGLN  120
QMRGAICDMV AIARYLNVTL IVPELDKASF WADPSEFQDI FDVDHFITSL RDEVRILKEL  180
PPRLKRRVEL GLFYSLPPIS WSDISYYQNQ ILPLLQKYKV VHLNRTDARL ANNGLPLEIQ  240
KLRCKVNFSA LRFMSQIEEL GRKIVSILRE NGPFVVLHLR YEMDMLAFSG CSHGCNSEEV  300
NELTRMRYAY PWWKEKIIDS DLKRKEGLCP LTPEETALIL TALGIDHDVQ IYIAAGEIYG  360
GGRRLASLAA AFPNLVKKEK LLDPSDLKYF QNHSSQMAAL DYLVSLESDI FVPTYDGNMA  420
KVVEGHRRYL GYKKTISLDR KLLVDLIDRH YAGSLSWDEF ASTVKETHAD RMGSARERLV  480
IPDRPKEEDY FFANPHECLQ PLVEPLRIT                                   509

SEQ ID NO: 27          moltype = AA  length = 502
FEATURE                Location/Qualifiers
source                 1..502
                       mol_type = protein
                       organism = synthetic construct
SEQUENCE: 27
MEFRSENAQN RCDKLPGQVI PKTRLQIWFI RVCSSILIWT CLVQLVTVGE LWHPRLLAGL  60
SNRSNGSSKI STEERAVPSL LPLLPARNYT SNGFLKVSCN GGLNQMRAAI CDMVTVARLL  120
NLTLVVPELD KTSFWADPSN FEDIFNVRHF IDSLRDEVHI VKRIPKKFIR RYGYQSLQMP  180
PVSWSSEKYY LEQILPLFNK HKLIHFNRTD TRLANNMIPL DLQKLRCRVN FQALRFTPQI  240
EALGQKLVDI LQGKGPFIAL HLRYEMDMLA FSGCTHGCTE EEAVKLKRLR YAFPWWREKE  300
IVSEERRSLG LCPLTPEEAV LVLQALNFDK DTQIYIASGE IYGSERRLAV LRASFPRIVK  360
KEMLLDPGEL QQFQNHSSQM AALDFIVSVA SSVFIPTYDG NMAKLVEGHR RYLGFRKTLQ  420
LDRRKIVELI DSYQNKTLSW EDFVGAMRLT HERRTGQPTG RKVIADKPKE EDYFYANPHE  480
CLCESPNCDN LQPPGNLTEK FR                                          502

SEQ ID NO: 28          moltype = AA  length = 499
FEATURE                Location/Qualifiers
source                 1..499
                       mol_type = protein
                       organism = synthetic construct
```

```
SEQUENCE: 28
MGWKTLGGES RKRIEKLRSS MVSRSRMKLW MIRATTSLLL WTCVVQLTAL GELWGPRVLK  60
GWPSCFTQDS VMDIKMTPAL PARVLPPKRV YKNNGYLMVS CNGGLNQMRA AICDMVAIAR  120
YLNVTLIVPE LDKTSFWADP SEFQDIFDVD HFISSLRDEV RILKELPPRI KRRVELGMFY  180
TMAPVSWSDI SYYHNQILPL VQKYKVVHLN RTDARLANNG QPLEIQKLRC RVNFGALRFT  240
PQIEELGRRV VKLLRQNGPF LVLHLRYEMD MLAFSGCSQG CNNEEVDELT RMRYAYPWWK  300
EKIINSDLKR KDGLCPLTPE ETALTLRALD IDHDIQIYIA AGEIYGGERR MASLAAAYPK  360
LVRKETLLSQ SDLGYFKNHS SQMAALDYLV SLESDIFVPT YDGNMAKVVE GHRRFLGLKK  420
TILLDRKLLV DLIDQYNHGS LNWDEFSIAV KNAHADRMGN ATKRLVIPDR PKEEDYFYAN  480
PEECLRFSEV SSEELLSII                                              499

SEQ ID NO: 29          moltype = AA  length = 501
FEATURE                Location/Qualifiers
source                 1..501
                       mol_type = protein
                       organism = synthetic construct
SEQUENCE: 29
MKSVRVEGRG RKESWSMKFV DEKKEAKSRF MVSRSRMMLW IIRGMTTLLL WTFVIRLLTM  60
GEVWGPRLLK SWPSCMFTEV NLSDAQPKVF QPPKRVYKNN GYLLVSCNGG LNQMRGAICD  120
MVAVARHLNV TLIVPELDKT SFWADPSEFK DIFDVDHFIA SLRDEVRILK ELPPRLKRRV  180
ELGLYHSLPP ISWSDISYYH NQILPLLQKY KVVHLNRTDA RLANNGLPLE IQKLRCRVNF  240
SALKFTSQIE TLGRKVVSIL RQNGPFVVLH LRYEMDMLAF SGCSHGCNNE EVEHLTRMRY  300
AYPWWKEKVI DSDFKRREGL CPLTPEETAQ VLTALGINRD VQIYIAAGEI YGGARRMASL  360
AAAFPNLVRK ENLLDPSDLR YFQNHSSQMA ALDYLVSLQS DIFVPTYDGN MAKVVEGHRR  420
YLGFKKTISL NRKLLVDLID RYHGGLLSWD DFSSMVKESH ADRMGSAKQR LVIPDRPKEE  480
DYFYANPHEC FQPLVEQYTL E                                           501

SEQ ID NO: 30          moltype = DNA  length = 39
FEATURE                Location/Qualifiers
source                 1..39
                       mol_type = other DNA
                       organism = synthetic construct
SEQUENCE: 30
taagaaggag atataccatg accagcagtc agctgaaag                       39

SEQ ID NO: 31          moltype = DNA  length = 41
FEATURE                Location/Qualifiers
source                 1..41
                       mol_type = other DNA
                       organism = synthetic construct
SEQUENCE: 31
ctgttcgact taagcattac ttattcagca gcggacccac a                     41

SEQ ID NO: 32          moltype = DNA  length = 64
FEATURE                Location/Qualifiers
source                 1..64
                       mol_type = other DNA
                       organism = synthetic construct
SEQUENCE: 32
taagaaggag atataccatg gatgatctct cttctctaaa actgggtgtt aaattttttc  60
aagc                                                              64

SEQ ID NO: 33          moltype = DNA  length = 48
FEATURE                Location/Qualifiers
source                 1..48
                       mol_type = other DNA
                       organism = synthetic construct
SEQUENCE: 33
ctgttcgact taagcattac tttcccttaa caaacggcgg acttccac              48

SEQ ID NO: 34          moltype = DNA  length = 46
FEATURE                Location/Qualifiers
source                 1..46
                       mol_type = other DNA
                       organism = synthetic construct
SEQUENCE: 34
ttaagaagga gatataccat ggctaccaat attgagcagc agcagc                46

SEQ ID NO: 35          moltype = DNA  length = 46
FEATURE                Location/Qualifiers
source                 1..46
                       mol_type = other DNA
                       organism = synthetic construct
SEQUENCE: 35
ttaagaagga gatataccat ggctaccaat attgagcagc agcagc                46

SEQ ID NO: 36          moltype = DNA  length = 60
FEATURE                Location/Qualifiers
source                 1..60
```

```
                        mol_type = other DNA
                        organism = synthetic construct
SEQUENCE: 36
ttaagaagga gatataccat ggattcacaa tttcagcagc ttcactttgt tatgataccc  60

SEQ ID NO: 37           moltype = DNA  length = 61
FEATURE                 Location/Qualifiers
source                  1..61
                        mol_type = other DNA
                        organism = synthetic construct
SEQUENCE: 37
ctgttcgact taagcattag cttaatgcta acctatcctt tacttgttca atgatgtctt  60
g                                                                  61

SEQ ID NO: 38           moltype = DNA  length = 47
FEATURE                 Location/Qualifiers
source                  1..47
                        mol_type = other DNA
                        organism = synthetic construct
SEQUENCE: 38
taagaaggag atataccatg ggttcagaat ctcaagtgca gcttcac                47

SEQ ID NO: 39           moltype = DNA  length = 54
FEATURE                 Location/Qualifiers
source                  1..54
                        mol_type = other DNA
                        organism = synthetic construct
SEQUENCE: 39
gttcgactta agcatcactt cctttctttc aaaatgtctt ggattagtaa cgtc        54

SEQ ID NO: 40           moltype = DNA  length = 54
FEATURE                 Location/Qualifiers
source                  1..54
                        mol_type = other DNA
                        organism = synthetic construct
SEQUENCE: 40
taagaaggag atataccatg gccaacttag ctcaaaacct tcattttgtc ttgc        54

SEQ ID NO: 41           moltype = DNA  length = 60
FEATURE                 Location/Qualifiers
source                  1..60
                        mol_type = other DNA
                        organism = synthetic construct
SEQUENCE: 41
ttctgttcga cttaagcatc atttacttgt cccatgggcc ataatttctt gaattaggtg  60

SEQ ID NO: 42           moltype = DNA  length = 36
FEATURE                 Location/Qualifiers
source                  1..36
                        mol_type = other DNA
                        organism = synthetic construct
SEQUENCE: 42
taagaaggag atataccatg tcccgaatca gcggtc                            36

SEQ ID NO: 43           moltype = DNA  length = 46
FEATURE                 Location/Qualifiers
source                  1..46
                        mol_type = other DNA
                        organism = synthetic construct
SEQUENCE: 43
tgttcgactt aagcatcaaa cattttcttg attgttcaat ttccgg                 46

SEQ ID NO: 44           moltype = DNA  length = 48
FEATURE                 Location/Qualifiers
source                  1..48
                        mol_type = other DNA
                        organism = synthetic construct
SEQUENCE: 44
taagaaggag atataccatg ggaactattg caaacggaga aattgccc               48

SEQ ID NO: 45           moltype = DNA  length = 57
FEATURE                 Location/Qualifiers
source                  1..57
                        mol_type = other DNA
                        organism = synthetic construct
SEQUENCE: 45
gttcgactta agcatcaaca agtggtaatt gatctaattt ctgaaatgaa ttcgtcg     57

SEQ ID NO: 46           moltype = DNA  length = 47
```

```
FEATURE                Location/Qualifiers
source                 1..47
                       mol_type = other DNA
                       organism = synthetic construct
SEQUENCE: 46
aagaaggaga tatacaatgg attctcaatt tcaacaattg cattttg               47

SEQ ID NO: 47          moltype = DNA  length = 62
FEATURE                Location/Qualifiers
source                 1..62
                       mol_type = other DNA
                       organism = synthetic construct
SEQUENCE: 47
cagcagccta ggttaattta agacaaagct aatctatctt taacttgttc aattatatct  60
tg                                                                 62

SEQ ID NO: 48          moltype = DNA  length = 63
FEATURE                Location/Qualifiers
source                 1..63
                       mol_type = other DNA
                       organism = synthetic construct
SEQUENCE: 48
gttgaaattg agaatccatg gtatatctcc ttcttaaagt taaacaaaat tatttctaga  60
ggg                                                                63

SEQ ID NO: 49          moltype = DNA  length = 43
FEATURE                Location/Qualifiers
source                 1..43
                       mol_type = other DNA
                       organism = synthetic construct
SEQUENCE: 49
gatagattag ctttgtctta agaattcgag ctccgtcgac aag                    43

SEQ ID NO: 50          moltype = DNA  length = 44
FEATURE                Location/Qualifiers
source                 1..44
                       mol_type = other DNA
                       organism = synthetic construct
SEQUENCE: 50
gtatatctcc ttcttaaagt taaacaaaat tatttctaga gggg                   44

SEQ ID NO: 51          moltype = DNA  length = 31
FEATURE                Location/Qualifiers
source                 1..31
                       mol_type = other DNA
                       organism = synthetic construct
SEQUENCE: 51
tgcttaagtc gaacagaaag taatcgtatt g                                 31

SEQ ID NO: 52          moltype = DNA  length = 50
FEATURE                Location/Qualifiers
source                 1..50
                       mol_type = other DNA
                       organism = synthetic construct
SEQUENCE: 52
taataaggag atataccatg gaggttagat ccgagagtgt acagttgagg             50

SEQ ID NO: 53          moltype = DNA  length = 57
FEATURE                Location/Qualifiers
source                 1..57
                       mol_type = other DNA
                       organism = synthetic construct
SEQUENCE: 53
gattactttc tgttcgatca tctcgaagtt tctgttgaat tgacggtacc taatacg     57

SEQ ID NO: 54          moltype = DNA  length = 54
FEATURE                Location/Qualifiers
source                 1..54
                       mol_type = other DNA
                       organism = synthetic construct
SEQUENCE: 54
taataaggag atataccatg tgtgaattag atgagaacag ggaagagagg gaga        54

SEQ ID NO: 55          moltype = DNA  length = 59
FEATURE                Location/Qualifiers
source                 1..59
                       mol_type = other DNA
                       organism = synthetic construct
SEQUENCE: 55
```

```
gattactttc tgttcgatca tgtaattctt aatggttcaa ccaagggttg caaacactc   59

SEQ ID NO: 56           moltype = DNA  length = 60
FEATURE                 Location/Qualifiers
source                  1..60
                        mol_type = other DNA
                        organism = synthetic construct
SEQUENCE: 56
ataaggagat ataccatgga gtttagatct gagaatgcac agaataggtg tgataaactg  60

SEQ ID NO: 57           moltype = DNA  length = 49
FEATURE                 Location/Qualifiers
source                  1..49
                        mol_type = other DNA
                        organism = synthetic construct
SEQUENCE: 57
cgattacttt ctgttcgatt accggaactt ctcagttaaa ttgcccggg              49

SEQ ID NO: 58           moltype = DNA  length = 49
FEATURE                 Location/Qualifiers
source                  1..49
                        mol_type = other DNA
                        organism = synthetic construct
SEQUENCE: 58
taataaggag atataccatg ggtggaaga cattaggagg tgagagtag              49

SEQ ID NO: 59           moltype = DNA  length = 60
FEATURE                 Location/Qualifiers
source                  1..60
                        mol_type = other DNA
                        organism = synthetic construct
SEQUENCE: 59
tactttctgt tcgatcagat gatgcttaga agttcttcag atgaaacttc tgaaaatcgc  60

SEQ ID NO: 60           moltype = DNA  length = 46
FEATURE                 Location/Qualifiers
source                  1..46
                        mol_type = other DNA
                        organism = synthetic construct
SEQUENCE: 60
aataaggaga tataccatga aaagtgtgag agtggagggg agaggg                 46

SEQ ID NO: 61           moltype = DNA  length = 57
FEATURE                 Location/Qualifiers
source                  1..57
                        mol_type = other DNA
                        organism = synthetic construct
SEQUENCE: 61
gattactttc tgttcgatca ttcaagtgta tattgttcaa ccaagggctg aaaacac     57

SEQ ID NO: 62           moltype = DNA  length = 43
FEATURE                 Location/Qualifiers
source                  1..43
                        mol_type = other DNA
                        organism = synthetic construct
SEQUENCE: 62
tttaacttta ataaggagat ataccatggc gacccatacc ccg                    43

SEQ ID NO: 63           moltype = DNA  length = 39
FEATURE                 Location/Qualifiers
source                  1..39
                        mol_type = other DNA
                        organism = synthetic construct
SEQUENCE: 63
catggtatat ctccttttac tcgagcgctt tcacttcgg                         39

SEQ ID NO: 64           moltype = DNA  length = 59
FEATURE                 Location/Qualifiers
source                  1..59
                        mol_type = other DNA
                        organism = synthetic construct
SEQUENCE: 64
agttgctggc gctgattggc atcgttttag agctagaaat agcaagttaa aataaggct   59

SEQ ID NO: 65           moltype = DNA  length = 51
FEATURE                 Location/Qualifiers
source                  1..51
                        mol_type = other DNA
                        organism = synthetic construct
```

-continued

```
SEQUENCE: 65
aaacgatgcc aatcagcgcc agcactagta ttatacctag gactgagcta g          51

SEQ ID NO: 66           moltype = DNA  length = 24
FEATURE                 Location/Qualifiers
source                  1..24
                        mol_type = other DNA
                        organism = synthetic construct
SEQUENCE: 66
cctcgtgtca ggggatccat tttc                                         24

SEQ ID NO: 67           moltype = DNA  length = 50
FEATURE                 Location/Qualifiers
source                  1..50
                        mol_type = other DNA
                        organism = synthetic construct
SEQUENCE: 67
tgatccggca aacaaaccac cgctggtagc cacggcgcgg ttttcagtgc            50

SEQ ID NO: 68           moltype = DNA  length = 54
FEATURE                 Location/Qualifiers
source                  1..54
                        mol_type = other DNA
                        organism = synthetic construct
SEQUENCE: 68
gctaccagcg gtggtttgtt tgccggatca ttgagcagga atatcgtgat cagg       54

SEQ ID NO: 69           moltype = DNA  length = 23
FEATURE                 Location/Qualifiers
source                  1..23
                        mol_type = other DNA
                        organism = synthetic construct
SEQUENCE: 69
tttacccaaa aacatttcgg gcg                                          23
```